US007304077B2

(12) United States Patent
Sanganee et al.

(10) Patent No.: US 7,304,077 B2
(45) Date of Patent: *Dec. 4, 2007

(54) CHEMICAL COMPOUNDS

(75) Inventors: Hitesh Sanganee, Loughborough (GB); Brian Springthorpe, Loughborough (GB)

(73) Assignee: AstraZeneca AB, Södertälje (SE)

(*) Notice: Subject to any disclaimer, the term of this patent is extended or adjusted under 35 U.S.C. 154(b) by 0 days.

This patent is subject to a terminal disclaimer.

(21) Appl. No.: 10/344,758

(22) PCT Filed: Aug. 30, 2001

(86) PCT No.: PCT/SE01/01869

§ 371 (c)(1), (2), (4) Date: Feb. 13, 2003

(87) PCT Pub. No.: WO02/20484

PCT Pub. Date: Mar. 14, 2002

(65) Prior Publication Data

US 2004/0102432 A1 May 27, 2004

(51) Int. Cl.
*A61K 31/445* (2006.01)
*C07D 211/14* (2006.01)

(52) U.S. Cl. ...................................... 514/327; 546/216
(58) Field of Classification Search ................ 514/327; 546/216
See application file for complete search history.

(56) References Cited

U.S. PATENT DOCUMENTS

| 4,335,127 | A | 6/1982 | Vandenberk et al. | |
|---|---|---|---|---|
| 4,853,393 | A | 8/1989 | Zimmermann | |
| 5,143,923 | A | 9/1992 | Hrib et al. | |
| 5,210,086 | A | 5/1993 | George et al. | |
| 6,140,344 | A | 10/2000 | Gong et al. | |
| 6,518,286 | B1 | 2/2003 | Baxter et al. | |
| 2003/0050309 | A1 | 3/2003 | Aquila et al. | 514/211.01 |
| 2003/0134840 | A1 | 7/2003 | Baxter et al. | |

FOREIGN PATENT DOCUMENTS

| EP | 0124476 | 11/1984 |
|---|---|---|
| EP | 0184258 | 5/1986 |
| EP | 0288563 | 11/1988 |
| EP | 0 429 341 A3 | 5/1991 |
| EP | 0 429 341 A2 | 5/1991 |
| EP | 0 515 240 A1 | 11/1992 |
| EP | 0661266 | 7/1995 |
| EP | 0903349 | 3/1999 |
| FR | 2 675 801 A1 | 10/1992 |
| FR | 2724382 | 3/1996 |
| GB | 1 243 991 | 8/1971 |
| JP | 03264579 | 11/1991 |
| JP | 0904646 | 2/1997 |
| JP | 09077742 | 3/1997 |
| WO | WO 96/14317 | 5/1996 |
| WO | WO 96/29330 | 9/1996 |
| WO | WO 97/10207 | 3/1997 |
| WO | WO97/42956 | 11/1997 |
| WO | WO 97/49680 | 12/1997 |
| WO | WO99/04794 | 2/1999 |
| WO | WO 99/37617 | 7/1999 |
| WO | WO 99/37619 | 7/1999 |
| WO | WO99/38514 | 8/1999 |
| WO | WO00/29377 | 5/2000 |
| WO | WO00/35877 | 6/2000 |
| WO | WO 00/58305 | 10/2000 |
| WO | WO01/14333 | 3/2001 |
| WO | WO 01/92227 | 12/2001 |
| WO | WO 02/30899 | 4/2002 |
| WO | WO03/18566 | * 3/2003 |
| WO | WO 03/018556 | 3/2003 |

OTHER PUBLICATIONS

Emonds–alt et al. "Preparation of . . . " Ca 119:8684 (1993).*
Acs et al. "Preparation of n–4–piperidinylbutylcarboxamides . . . " CA 138:287532 (2003).*
Baxter "Preparation of piperidinyl compounds . . . " CA 133:266738 (2000).*
Chemical Abstracts, vol. 97, 1982, Printout for Vandenberk et al.
Herndon et al., "Ketanserin Analogues: Structure–Affinity Relationships for 5–HT.sub.2 and 5–HT.sub.1C Serotonin Receptor Binding", J. Med. Chem., vol. 35:4903–4910 (1992).
Hrib et al., "Benzisoxazole–and Benzisothiazole–3–carboxamides as Potential Atypical Antipsychotic Agents", J. Med. Chem., vol. 37:2308–2314 (1994).
C.G.M. Janssen et al., "Synthesis of .sup.3 H and .sup.14 C Ketanserin", Journal of Labelled Components and Radiopharmaceuticals, vol. XXV, No. 7, pp. 783–792 (1988).
Chem. Abstracts, Accession No. 1980:586265, Carissimi et al. Farmaco, Edizion Scientifica (1980), 35(6), 504–26.
King "Medicinal chemistry: principle and practice" pp. 206–209 (1994).*
Rubini et al. "Synthesis of isosteric methylen–oxy...." Tetrahedron v. 42, pp. 6039–45 (1986).*
Bundgaard, "Design of prodrugs", p. 1, 1986.
CAS printout for Kikuchi et al., Chem. Abs. 128:22926 (JP 09291090).
CAS printout for Takahashi et al., Chem. Abs. 128:294706 (JP 10077271).
Cohen et al., "Cytokine function: A study in biologic diversity", CA 125:3527, 1996.

(Continued)

*Primary Examiner*—Celia Chang
(74) *Attorney, Agent, or Firm*—Fish & Richardson P.C.

(57) ABSTRACT

The invention provides compounds of formula (I): as modulators of chemokine and H1 receptor activity. The compounds are especially useful in the treatment of asthma and rhinitis.

9 Claims, No Drawings

OTHER PUBLICATIONS

Ian T. Forbes et al., "(R)-3, N-Dimethyl-N-[1-methyl-3-(4-methyl-piperidin-1-yl)propyl]benzene-sulfonamide:The First Selective 5-$HT_7$ Receptor Antagonist" 41 Journal of Medicinal Chemistry 5, 655-657 (1998).

Jean-Luc Malleron et al., "New Indole Derivatives as Potent and Selective Serotonin Uptake Inhibitors" 36 J. Med. Chem. 1194-1202 (1993).

STN International, File Caplus, Caplus accession no. 1996:113480, Document no. 124:220549, Kharkovskij Farmatsevticheskij Institut: Piperdylamide of 3,5-dibromo-4-aminobenzene-sulfonylaminosuccinic acid which produces neuroptic and diruetic effects; & SU, A1, 1824396, 1993630.

* cited by examiner

CHEMICAL COMPOUNDS

CROSS REFERENCE TO RELATED APPLICATIONS

The present application is a national phase application under 35 U.S.C. Section 371 filed from International Patent Application PCT/SE01/01869, filed 30 Aug. 2001, which claims priority to United Kingdom patent application Serial No. 0021670.5, filed 4 Sep. 2000. The contents of these applications are incorporated herein by reference in their entirety.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794, WO00/29377, WO00/35877, WO0058305 and WO01/14333.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria. H1 antagonists are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

The present invention provides a compound of formula (I):

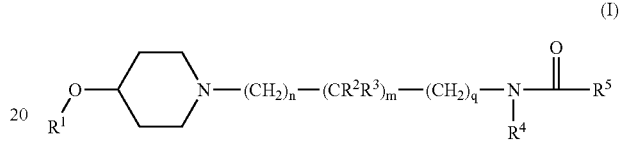

wherein
$R^1$ is phenyl optionally substituted by cyano, $S(O)_2(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy;
n is 0, 1, 2, 3 or 4; m is 0 or 1; when m is 0 then q is 0, and when m is 1 then q is 1, 2 or 3;
provided that n+m+q=1, 2, 3 or 4;
when $R^2$ and $R^3$ are, independently, hydrogen or $C_{1-6}$ alkyl, and $R^4$ is hydrogen, then $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being substituted at least once with a substituent selected from the group comprising: $C_{1-6}$ alkyl (substituted with $NH_2$, $CO_2(C_{1-6}$ alkyl), $S(O)_2(C_{1-6}$ alkyl), $NHS(O)_2(C_{1-6}$ alkyl) or $S(O)_2NR^{13}R^{14})$, $S(O)_2$ $(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), $C_{1-6}$ alkoxy (substituted with $C_{1-6}$ alkoxy, hydroxy, $CO_2(C_{1-6}$ alkyl), $NHC(O)O(C_{1-6}$ alkyl) or $NH_2$), $C_{2-6}$ alkenyl, pyrrolyl and $\Delta^3$-pyrrolinyl; and optionally flirter substituted with a substituent selected from the group comprising: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido $(S(O)_2NH_2)$, $(di)C_{1-6}$ alkylsulphonamido, phenyl, phenylamino, nitrophenyl, pyridyl, pyridylthio, benzodioxanyl, thienyl, furanyl, and $C(O)R^{10}$-substituted $C_{1-6}$ alkyl or $C_{1-6}$ alkoxy groups;
when $R^2$ and $R^3$ are, independently, hydrogen or $C_{1-6}$ alkyl, and $R^4$ is $C_{1-4}$ alkyl or $C_{3-6}$ cycloalkyl($C_{1-4}$ alkyl), then $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being optionally substituted by halogen, cyano, nitro, hydroxy, $C_{1-6}$ alkyl (optionally substituted with halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2$ $(C_{1-6}$ alkyl) or $S(O)_2NR^{13}R^{14})$, $C_{3-6}$ cycloalkyl, $C_{1-6}$ alkoxy (substituted with halogen, $C_{1-6}$ alkoxy, hydroxy, $C(O)R^{10}$, $CO_2(C_{1-6}$ alkyl), $NHC(O)O(C_{1-6}$ alkyl) or $NH_2$), $C_{2-6}$ alkenyl, $C_{1-6}$ alkoxycarbonyl, $NR^6R^7$, $C_{3-6}$ cycloalkylamino, $C_{1-6}$ alklylthio, $C_{1-6}$ alkylcarbonylamino, $C(O)NR^8R^9$, sulphonamido ($S(O)_2NH_2$), (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl;

and when $R^2$ is phenyl (optionally substituted with halogen, $C_{1-4}$ alkyl or $C_{1-4}$ alkoxy), $R^3$ is hydrogen or $C_{1-6}$ alkyl, and $R^4$ is hydrogen, $C_{1-4}$ alkyl or $C_{3-6}$ cycloalkyl($C_{1-4}$ alkyl), then $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being optionally substituted by halogen, cyano, nitro, hydroxy, $C_{1-6}$ alkyl (optionally substituted with halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2(C_{1-6}$ alkyl) or $S(O)_2NR^{13}R^{14}$), $C_{3-6}$ cycloalkyl, $C_{1-6}$ alkoxy (substituted with halogen, $C_{1-6}$ alkoxy, hydroxy, $C(O)R^{10}$, $CO_2(C_{1-6}$ alkyl), $NHC(O)O(C_{1-6}$ alkyl) or $NH_2$), $C_{2-6}$ alkenyl, $C_{1-6}$ alkoxycarbonyl, $NR^6R^7$, $C_{3-6}$ cycloalkylamino, $C_{1-6}$ alkylthio, $C_{1-6}$ alkylcarbonylamino, $C(O)NR^8R^9$, sulphonamido ($S(O)_2NH_2$), (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl;

or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, acetate, diacetate, fumarate, maleate, tartrate, citrate, oxalate, methanesulphonate or p-toluenesulphonate.

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl, iso-butyl or tert-butyl.

Alkenyl group are, for example, vinyl or alkyl.

Cycloalkyl is, for example, cyclopropyl, cyclopentyl or cyclohexyl; and cycloalkylalkyl is, for example cyclopropyhnethyl. Alkoxy includes methoxy, ethoxy, n-propoxy, iso-propoxy and tert-butoxy; alkoxycarbonyl includes methoxy- and ethoxy-, carbonyl; haloalkyl includes trifluoromethyl; haloalkoxy includes trifluoromethoxy; cycloalkylamino includes cyclopropyl-, cyclobutyl-, cyclopentyl- or cyclohexylamino; alkylthio includes methyl- or ethylthio; alkylthioalkyl includes methylthiomethyl; alkylcarbonylamino includes methyl- or ethylcarbonylamino; $C(O)NR^8R^9$ includes $C(O)NHCH_3$; dialkylsulphonamido includes dimethylsulphonamido and diethylsulphonamido; alkyl substituted with $NH_2$ includes $CH_2NH_2$; alkyl substituted with $CO_2$(alkyl) includes $CH_2CO_2CH_3$; alkyl substituted with $S(O)_2$(alkyl) includes $CH_2S(O)_2CH_3$ and $CH_2S(O)_2CH_2CH_3$; alkyl substituted with $NHS(O)_2$(alkyl) includes $CH_2NHS(O)_2CH_3$; alkyl substituted with $S(O)_2NR^{13}R^{14}$ includes $CH_2S(O)_2N(CH_3)_2$; $S(O)_2$(alkyl) includes $S(O)_2CH_3$ and $S(O)_2CH_2CH_3$; $S(O)_2$(hydroxyalkyl) includes $S(O)_2CH_2CH_2OH$; $S(O)_2NH$(alkyl) includes $S(O)_2NHCH_3$; $NHC(O)$(alkyl) includes $NHC(O)CH_3$; $NHS(O)_2$(alkyl) includes $NHS(O)_2CH_3$; alkoxy substituted with alkoxy includes $O(CH_2)_2OCH_3$; alkoxy substituted with hydroxy includes $O(CH_2)_2OH$; alkoxy substituted with $CO_2$(alkyl) $OCH_2CO_2CH_3$; alkoxy substituted with $NHC(O)O$(alkyl) includes $OCH_2NHCO_2CH_3$; and alkoxy substituted with $NH_2$ includes $OCH_2NH_2$.

The 3- to 10-membered saturated or unsaturated ring system in the group $R^5$ may be monocyclic or polycyclic comprising 2 or more fused rings, examples of which include cyclobutyl, cyclopentyl, cyclohexyl, norbornylenyl, adamantyl, phenyl, naphthyl, furyl, thienyl, pyrrolyl, 2,5-dihydro-1H-pyrrolyl (also known as $\Delta^3$-pyrroline), thiazolyl, isothiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl (for example a pyrimidinedione), pyrazinyl, pyridazinyl, indolyl, 2,3-dihydroindolyl, benzo[b]furyl, benz[b]thienyl, 2,3-dihydrobenz[b]thienyl (for example in 1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl, benzo[1,2,3]thiadiazolyl, 2,1,3-benzothiadiazolyl, benzofurazan, quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), a pyrazolopyrimidinyl, a thienopyrimidinyl, athiazolopyrimidinyl, quinolinyl, isoquinolinyl (for example in 2H-isoquinolin-1-one-yl), quinoxalinyl (for example 2,4-dioxo-3,4-dihydroquinazolinyl), a naphthyridinyl (for example [1,6] naphthyridinyl or [1,8]naphthyridinyl or in 1H-[1,8] naphthyridin-4-one-yl), chromonyl, 1,3-benzodioxolyl, a benzothiazinyl (for example in 4H-benzo[1,4]thiazin-3-one-yl), benzo[d]imidazo[2,1-b]thiazol-2-yl or dibenzothiophenyl; or an N-oxide thereof, or an S-oxide or S-dioxide thereof.

Alternatively, the 3- to 10-membered saturated or unsaturated ring system in the group $R^5$ may be monocyclic or polycyclic comprising 2 or more fused rings, examples of which include cyclobutyl, cyclopentyl, cyclohexyl, norbomylenyl, adamantyl, piperidyl, phenyl, naphthyl, naphthyridinyl, 1,3-benzodioxolyl, pyrazolyl, furanyl, pyridyl, thienyl, indolyl, benzthiazolyl, benzthienyl, 1,2,3-benzthiadiazolyl, benzoxazolyl, benzothiazolyl, chromonyl, imidazolyl, quinolinyl, isoquinolinyl, benzimidazolyl, pyrimidinyl, pyrazolopyrimidinyl, thienopyrimidinyl, thiazolopyrimidinyl, pyrimidinedione, pyrazinyl, pyridazinyl, purinyl, quinoxalinyl, thiazolyl, isothiazolyl and 2,4-dioxo-3,4-dihydro-quinazolinyl. $\Delta^3$-Pyrroline is also known as 2,5-dihydro-1H-pyrrole and has the structure:

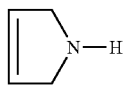

In one aspect m and q are both 0.

In another aspect the present invention provides a compound of formula (I) wherein $R^1$ is phenyl optionally substituted by cyano, $S(O)_2(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy; n is 0, 1, 2, 3 or 4; m is 0 or 1; when m is 0 then q is 0, and when m is 1 then q is 1, 2 or 3; provided that n+m+q=1, 2, 3 or 4; $R^2$ and $R^3$ are, independently, hydrogen or $C_{1-6}$ alkyl; $R^4$ is hydrogen; $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being substituted at least once with a substituent selected from the group comprising: $C_{1-6}$ alkyl (substituted with $NH_2$, $CO_2(C_{1-6}$ alkyl), $S(O)_2(C_{1-6}$ alkyl), $NHS(O)_2(C_{1-6}$ alkyl) or $S(O)_2NR^{13}R^{14}$), $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), $C_{1-6}$ alkoxy (substituted with $C_{1-6}$ alkoxy, hydroxy, $CO_2(C_{1-6}$ alkyl), $NHC(O)O(C_{1-6}$ alkyl) or $NH_2$), $C_{2-6}$ alkenyl, pyrrolyl and $\Delta^3$-pyrrolinyl; and optionally further substituted with a substituent selected from the group comprising: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido ($S(O)_2NH_2$), (di)$C_{1-6}$ alkylsulphonamido, phenyl, phenylamino, nitrophenyl, pyridyl, pyridylthio, benzodioxanyl, thienyl, furanyl, and $C(O)R^{10}$-substituted $C_{1-6}$ alkyl or $C_{1-6}$ alkoxy groups; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

In a further aspect the present invention provides a compound of formula (I) wherein $R^1$ is phenyl optionally substituted by cyano, $S(O)_2(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy; n is 0, 1, 2, 3 or 4; m is 0 or 1; when m is 0 then q is 0, and when m is 1 then q is 1, 2 or 3; provided that n+m+q=1, 2, 3 or 4; $R^2$ and $R^3$ are, independently, hydrogen or $C_{1-6}$ alkyl; $R^4$ is $C_{1-4}$ alkyl or $C_{3-6}$ cycloalkyl($C_{1-4}$ alkyl); $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being optionally substituted by halogen, cyano, nitro, hydroxy, $C_{1-6}$ alkyl (optionally substituted with halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2(C_{1-6}$ alkyl) or $S(O)_2NR^{13}R^{14}$), $C_{3-6}$ cycloalkyl, $C_{1-6}$ alkoxy (substituted with halogen, $C_{1-6}$ alkoxy, hydroxy, $C(O)R^{10}$, $CO_2(C_{1-6}$ alkyl), $NHC(O)O(C_{1-6}$ alkyl) or $NH_2$), $C_{2-6}$ alkenyl, $C_{1-6}$ alkoxycarbonyl, $NR^6R^7$, $C_{3-6}$ cycloalkylamino, $C_{1-6}$-alkylthio, $C_{1-6}$ alkylcarbonylamino, $C(O)NR^8R^9$, sulphonamido ($S(O)_2NH_2$), (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

In a still further aspect the present invention provides a compound of formula (I) wherein $R^1$ is phenyl optionally substituted by cyano, $S(O)_2(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy; n is 0, 1, 2, 3 or 4; m is 1; q is 1; provided that n+m+q=2, 3 or 4; $R^2$ is phenyl (optionally substituted with halogen, $C_{1-4}$ alkyl or $C_{1-4}$ alkoxy); $R^3$ is hydrogen or $C_{1-6}$ alkyl; $R^4$ is hydrogen, $C_{1-4}$ alkyl or $C_{3-6}$ cycloalkyl($C_{1-4}$ alkyl); $R^5$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being optionally substituted by halogen, cyano, nitro, hydroxy, $C_{1-6}$ alkyl (optionally substituted with halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2(C_{1-6}$ alkyl) or $S(O)_2NR^{13}R^{14}$), $C_{3-6}$ cycloalkyl, $C_{1-6}$ alkoxy (substituted with halogen, $C_{1-6}$ alkoxy, hydroxy, $C(O)R^{10}$, $CO_2(C_{1-6}$ alkyl), $NHC(O)O(C_{1-6}$ alkyl) Or $NH_2$), $C_{2-6}$ alkenyl, $C_{1-6}$ alkoxycarbonyl, $NR^6R^7$, $C_{3-6}$ cycloalkylamino, $C_{1-6}$ alkylthio, $C_{1-6}$ alkylcarbonylamino, $C(O)NR^8R^9$, sulphonamido ($S(O)_2NH_2$), (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

In another aspect $R^1$ is phenyl optionally substituted by halogen (such as chloro or fluoro), $C_{1-4}$ alkyl (such as methyl) or $C_{1-4}$ alkoxy (such as methoxy).

In a further aspect n is 2.

In yet another aspect $R^2$ is hydrogen.

In a still further aspect $R^3$ is hydrogen.

In another aspect $R^4$ is hydrogen or $C_{1-4}$ alkyl; and $R^1$ is a 3- to 10-membered saturated or unsaturated ring system which may comprise up to two ring carbon atoms that form carbonyl groups and which may comprise up to 4 ring heteroatoms independently selected from nitrogen, oxygen and sulphur, the ring system being substituted by at least one of $C_{1-6}$ alkyl (substituted with $S(O)_2(C_{1-6}$ alkyl), $NHS(O)_2(C_{1-6}$ alkyl) or $S(O)_2NR^{13}R^{14}$), $S(O)_2(C_{1-6}$ alkyl), $S(O)_2NH(C_{1-6}$ alkyl), $NHC(O)(C_{1-6}$ alkyl) or $NHS(O)_2(C_{1-6}$ alkyl); and optionally further substituted with a substituent selected from the group comprising: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alklylthio, $C_{1-6}$ alkylthio($C_{1-6}$ alkyl), $C_{1-6}$ alkylcarbonylamino, $C(O)NR^8R^9$, sulphonamido ($S(O)_2NH_2$), (di)$C_{1-6}$ alkylsulphonamido and $C(O)R^{10}$-substituted $C_{1-6}$ alkyl or $C_{1-6}$ alkoxy groups; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

In yet another aspect $R^4$ is hydrogen or $C_{1-4}$ alkyl; and $R^5$ is phenyl substituted by at least one of $C_{1-6}$ alkyl (substituted with $S(O)_2(C_{1-6}$ alkyl), $NHS(O)_2(C_{1-6}$ alkyl) or $S(O)_2NR^{13}R^{14}$), $S(O)_2(C_{1-6}$ alkyl), $S(O)_2NH(C_{1-6}$ alkyl), $NHC(O)(C_{1-6}$ alkyl) or $NHS(O)_2(C_{1-6}$ alkyl); and optionally further substituted with a substituent selected from the group comprising: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido ($S(O)_2NH_2$), (di)$C_{1-6}$ alkylsulphonamido and $C(O)R^{10}$-substituted $C_{1-6}$ alkyl or $C_{1-6}$ alkoxy groups; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

In a further aspect of the invention $R^4$ is hydrogen.

In a still further aspect $R^5$ is phenyl mono-substituted by $C_{1-6}$ alkyl (substituted with $S(O)_2(C_{1-6}$ alkyl), $NHS(O)_2$ ($C_{1-6}$ alkyl) or $S(O)_2NR^{13}R^{14}$), $S(O)_2(C_{1-6}$ alkyl), $S(O)_2NH$ ($C_{1-6}$ alkyl), $NHC(O)(C_{1-6}$ alkyl) or $NHS(O)_2(C_{1-6}$ alkyl); and $R^{13}$ and $R^{14}$ are independently hydrogen or $C_{1-6}$ alkyl.

In another aspect the invention provides any compound described in a Table or an Example herein, or a pharmaceutically acceptable salt thereof.

Compounds of the invention are listed in Table I. All the compounds in Table I are compounds of formula (I) wherein m and q are both 0.

TABLE I

| Compound No. | $R^1$ | n | $R^4$ | $R^5$ | M + H |
|---|---|---|---|---|---|
| 1 | 3,4-$Cl_2$—$C_6H_3$ | 2 | H | 4-$CH_2NH_2$—$C_6H_4$ | 422 |
| 2 | 3,4-$Cl_2$—$C_6H_3$ | 2 | H | 3,4-$(S(O)_2CH_3)_2$—$C_6H_3$ | 549 |
| 3 | 3,4-$Cl_2$—$C_6H_3$ | 2 | H | 3-$S(O)_2CH_2CH_2CH_3$—$C_6H_4$ | 499 |
| 4 | 3,4-$Cl_2$—$C_6H_3$ | 2 | H | 3-$S(O)_2CH_2CH(CH_3)_2$—$C_6H_4$ | 513 |
| 5 | 3,4-$Cl_2$—$C_6H_3$ | 2 | H | 3-$CH_2S(O)_2CH_3$—$C_6H_4$ | 485 |
| 6 | 3,4-$Cl_2$—$C_6H_3$ | 2 | H | 3-$S(O)_2CH_2CH_3$—$C_6H_4$ | 485 |
| 7 | 3,4-$Cl_2$—$C_6H_3$ | 2 | H | 4-$CH_2S(O)_2CH_3$—$C_6H_4$ | 485 |
| 8 | 3,4-$Cl_2$—$C_6H_3$ | 2 | H | 4-(pyrrol-1-yl)—$C_6H_4$ | 458 |
| 9 | 3,4-$Cl_2$—$C_6H_3$ | 2 | H | 3-$S(O)_2NHCH_3$—$C_6H_4$ | 486 |
| 10 | 3,4-$Cl_2$—$C_6H_3$ | 2 | H | 2-$NH_2$-5-$NHC(O)CH_3$—$C_6H_3$ | 465 |
| 11 | 3,4-$Cl_2$—$C_6H_3$ | 2 | H | 3-$NHC(O)CH_3$—$C_6H_4$ | 450 |
| 12 | 3,4-$Cl_2$—$C_6H_3$ | 2 | H | 3-$O(CH_2)_2OCH_3$—$C_6H_4$ | 467 |
| 13 | 3,4-$Cl_2$—$C_6H_3$ | 2 | H | 3-$S(O)_2CH_3$-4-$NH_2$—$C_6H_3$ | 486 |
| 14 | 3,4-$Cl_2$—$C_6H_3$ | 2 | H | 4-$CH=CH_2$—$C_6H_4$ | 419 |
| 15 | 3,4-$F_2$—$C_6H_3$ | 2 | $CH_2$-cyclopropyl | 3-$OCH_3$-4-F—$C_6H_3$ | |
| 16 | 3,4-$F_2$—$C_6H_3$ | 2 | H | 3-$S(O)_2CH_3$—$C_6H_4$ | |
| 17 | 3,4-$Cl_2$—$C_6H_3$ | 3 | H | 2-($\Delta^3$-pyrrolin-1-yl)-benzthiazol-6-yl | |
| 18 | 3,4-$F_2$—$C_6H_3$ | 2 | $CH_3$ | 3-$OCH_3$—$C_6H_4$ | |
| 19 | 3,4-$Cl_2$—$C_6H_3$ | 2 | H | 3-$S(O)_2CH_3$—$C_6H_4$ | |
| 20 | 3,4-$Cl_2$—$C_6H_3$ | 3 | H | 3-$S(O)_2CH_3$—$C_6H_4$ | |
| 21 | 3,4-$Cl_2$—$C_6H_3$ | 2 | H | 3-$O(CH_2)_2OH$—$C_6H_4$ | |
| 22 | 3,4-$Cl_2$—$C_6H_3$ | 2 | H | 3-$S(O)_2(CH_2)_2OH$—$C_6H_4$ | |
| 23 | 3,4-$Cl_2$—$C_6H_3$ | 2 | H | 3-$O(CH_2)_2NHC(O)$—$OC(CH_3)_3$—$C_6H_4$ | |
| 24 | 3,4-$Cl_2$—$C_6H_3$ | 2 | H | 3-$NHS(O)_2CH_3$—$C_6H_4$ | |
| 25 | 3,4-$Cl_2$—$C_6H_3$ | 2 | H | 3-$O(CH_2)_2NH_2$—$C_6H_4$ | |

In a further aspect the present invention provides the compounds listed in Table II which are of formula (II):

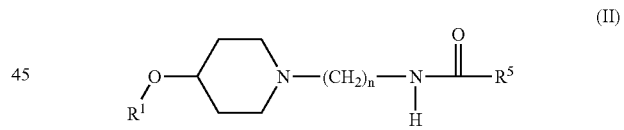

(II)

TABLE II

| Compound No. | $R^1$ | n | $R^5$ | M + H |
|---|---|---|---|---|
| 1 | 3,4-$Cl_2$—$C_6H_3$ | 2 | $C(CH_3)_2$(4-Cl—$C_6H_4$) | 469 |
| 2 | 3,4-$Cl_2$—$C_6H_3$ | 2 | $CH(CH_2CH_3)(C_6H_5)$ | 435 |
| 3 | 3,4-$Cl_2$—$C_6H_3$ | 2 | 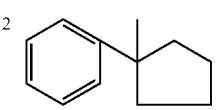 | 461 |
| 4 | 3,4-$Cl_2$—$C_6H_3$ | 2 | 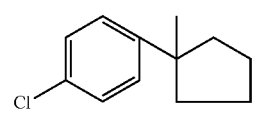 | 495 |

TABLE II-continued

| Compound No. | R¹ | n | R⁵ | M + H |
|---|---|---|---|---|
| 5 | 3,4-Cl$_2$—C$_6$H$_3$ | 2 | 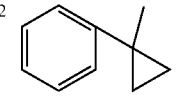 | 433 |
| 6 | 3,4-Cl$_2$—C$_6$H$_3$ | 2 | 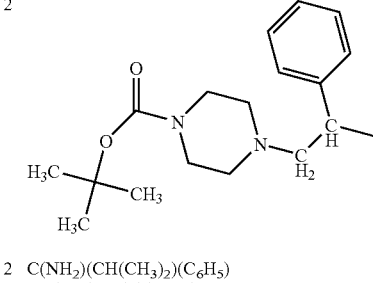 | 605 |
| 7 | 3,4-Cl$_2$—C$_6$H$_3$ | 2 | C(NH$_2$)(CH(CH$_3$)$_2$)(C$_6$H$_5$) | 464 |
| 8 | 3,4-Cl$_2$—C$_6$H$_3$ | 2 | CH(CH(CH$_3$)$_2$)(C$_6$H$_5$) | 449 |
| 9 | 3,4-Cl$_2$—C$_6$H$_3$ | 2 | CH$_2$(2,4-(OCH$_3$)$_2$—C$_6$H$_3$) | 467 |
| 10 | 3,4-Cl$_2$—C$_6$H$_3$ | 2 | CH$_2$(4-(OCH$_2$C$_6$H$_5$)—C$_6$H$_4$) | 513 |
| 11 | 3,4-Cl$_2$—C$_6$H$_3$ | 2 | CH$_2$(3-(OCH$_2$C$_6$H$_5$)—C$_6$H$_4$) | 513 |
| 12 | 3,4-Cl$_2$—C$_6$H$_3$ | 2 | CH$_2$(2-CH$_3$-Naphth-1-yl) | 471 |
| 13 | 3,4-Cl$_2$—C$_6$H$_3$ | 2 | CH$_2$(2,4,6-CH$_3$—C$_6$H$_2$) | 449 |
| 14 | 3,4-Cl$_2$—C$_6$H$_3$ | 2 | CH$_2$(2-(OCH$_2$CH$_3$)—C$_6$H$_4$) | 451 |
| 15 | 3,4-Cl$_2$—C$_6$H$_3$ | 2 | 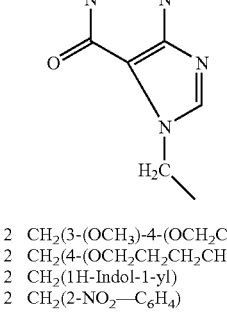 | 509 |
| 16 | 3,4-Cl$_2$—C$_6$H$_3$ | 2 | CH$_2$(3-(OCH$_3$)-4-(OCH$_2$CH$_3$)—C$_6$H$_3$) | 481 |
| 17 | 3,4-Cl$_2$—C$_6$H$_3$ | 2 | CH$_2$(4-(OCH$_2$CH$_2$CH$_3$)—C$_6$H$_4$) | 479 |
| 18 | 3,4-Cl$_2$—C$_6$H$_3$ | 2 | CH$_2$(1H-Indol-1-yl) | 446 |
| 19 | 3,4-Cl$_2$—C$_6$H$_3$ | 2 | CH$_2$(2-NO$_2$—C$_6$H$_4$) | 452 |
| 20 | 3,4-Cl$_2$—C$_6$H$_3$ | 2 | CH$_2$(3-Cl-4-OH—C$_6$H$_3$) | 457 |
| 21 | 3,4-Cl$_2$—C$_6$H$_3$ | 2 | CH$_2$(3,4-Cl$_2$—C$_6$H$_3$) | 475 |
| 22 | 3,4-Cl$_2$—C$_6$H$_3$ | 2 | CH$_2$(2,6-Cl$_2$—C$_6$H$_3$) | 475 |
| 23 | 3,4-Cl$_2$—C$_6$H$_3$ | 2 | CH$_2$(2-Br—C$_6$H$_4$) | 485 |
| 24 | 3,4-Cl$_2$—C$_6$H$_3$ | 2 | CH$_2$(1,4-(CH$_3$)$_2$-3-(CO$_2$H)-1H-Pyrrole-2-yl) | 468 |
| 25 | 3,4-Cl$_2$—C$_6$H$_3$ | 2 | 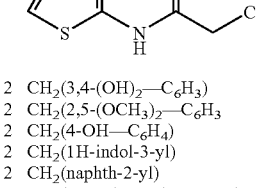 | 505 |
| 26 | 3,4-Cl$_2$—C$_6$H$_3$ | 2 | CH$_2$(3,4-(OH)$_2$—C$_6$H$_3$) | 439 |
| 27 | 3,4-Cl$_2$—C$_6$H$_3$ | 2 | CH$_2$(2,5-(OCH$_3$)$_2$—C$_6$H$_3$ | 467 |
| 28 | 3,4-Cl$_2$—C$_6$H$_3$ | 2 | CH$_2$(4-OH—C$_6$H$_4$) | 423 |
| 29 | 3,4-Cl$_2$—C$_6$H$_3$ | 2 | CH$_2$(1H-indol-3-yl) | 446 |
| 30 | 3,4-Cl$_2$—C$_6$H$_3$ | 2 | CH$_2$(naphth-2-yl) | 457 |
| 31 | 3,4-Cl$_2$—C$_6$H$_3$ | 2 | CH$_2$(3,4,5-(OCH$_3$)$_3$—C$_6$H$_2$) | 497 |
| 32 | 3,4-Cl$_2$—C$_6$H$_3$ | 2 | CH$_2$(2-(pyrazin-2-yl)-1,3-thiazol-4-yl) | 492 |
| 33 | 3,4-Cl$_2$—C$_6$H$_3$ | 2 | CH$_2$(5-(CH(CH$_3$)$_2$)-2-CH$_3$-1H-indol-3-yl) | 502 |
| 34 | 3,4-Cl$_2$—C$_6$H$_3$ | 2 | CH$_2$(5-(pyrrolidin-1-yl)-2H-tetrazol-2-yl) | 468 |
| 35 | 3,4-Cl$_2$—C$_6$H$_3$ | 2 | CH$_2$(5-(4-CH$_3$—C$_6$H$_4$)-2H-tetrazol-2-yl) | 489 |
| 36 | 3,4-Cl$_2$—C$_6$H$_3$ | 2 | CH$_2$(5-Cl-1-benzothien-3-yl) | 497 |
| 37 | 3,4-Cl$_2$—C$_6$H$_3$ | 2 | CH$_2$(5-CH$_3$-2-C$_6$H$_5$-1,3-thiazol-4-yl) | 504 |
| 38 | 3,4-Cl$_2$—C$_6$H$_3$ | 2 | CH$_2$(3-NO$_2$-4-Cl-5-CH$_3$-1H-pyrazol-1-yl) | 490 |
| 39 | 3,4-Cl$_2$—C$_6$H$_3$ | 2 | CH$_2$(4-NO$_2$-1-CH$_3$-1H-pyrazol-5-yl) | 456 |
| 40 | 3,4-Cl$_2$—C$_6$H$_3$ | 2 | CH$_2$(2-CF$_3$-1H-benzimidazol-1yl) | 515 |
| 41 | 3,4-Cl$_2$—C$_6$H$_3$ | 2 | CH$_2$(2-(ethylsulfanyl)-1H-benzimidazol-1-yl) | 507 |

TABLE II-continued

| Compound No. | R¹ | n | R⁵ | M + H |
|---|---|---|---|---|
| 42 | 3,4-Cl₂—C₆H₃ | 2 | CH₂(3-NO₂-5-CH₃-1H-pyrazol-1-yl) | 456 |
| 43 | 3,4-Cl₂—C₆H₃ | 2 | CH₂(2-CH₃-4-C₆H₅-1,3-thiazol-5-yl) | 504 |
| 44 | 3,4-Cl₂—C₆H₃ | 2 | CH₂(2-CH₃-4-(thien-2-yl)-1,3-thiazol-5-yl) | 510 |
| 45 | 3,4-Cl₂—C₆H₃ | 2 | CH₂(3,4-(NO₂)₂-5-CH₃-1H-pyrazol-1-yl) | 501 |
| 46 | 3,4-Cl₂—C₆H₃ | 2 | CH₂(4-(OCH₂CH₂CH(CH₃)₂)—C₆H₄) | 493 |
| 47 | 3,4-Cl₂—C₆H₃ | 2 | CH₂(2-(tert-Butylsulfanyl)-C₆H₄) | 495 |
| 48 | 3,4-Cl₂—C₆H₃ | 2 | CH₂(4-Cl-3,5-(CH₃)₂-1H-pyrazol-1-yl) | 459 |
| 49 | 3,4-Cl₂—C₆H₃ | 2 | *(structure: 1-methyl-7-ethylxanthine)* | 495 |
| 50 | 3,4-Cl₂—C₆H₃ | 2 | CH₂(4-NO₂-3,5-(CH₃)₂-1H-pyrazol-1-yl) | 470 |
| 51 | 3,4-Cl₂—C₆H₃ | 2 | CH₂(2,4-(NO₂)₂-1H-imidazol-1-yl) | 487 |
| 52 | 3,4-Cl₂—C₆H₃ | 2 | CH₂(3,5-(CH₃)₂-1H-pyrazol-1-yl) | 425 |
| 53 | 3,4-Cl₂—C₆H₃ | 2 | CH₂(2-CN—C₆H₄) | 432 |
| 54 | 3,4-Cl₂—C₆H₃ | 2 | 3-OH-pyridin-2-yl | 410 |
| 55 | 3,4-Cl₂—C₆H₃ | 2 | *(2-SH-3-methylpyridine)* | 426 |
| 56 | 3,4-Cl₂—C₆H₃ | 2 | *(2-NH₂-5-methylpyridine)* | 409 |
| 57 | 3,4-Cl₂—C₆H₃ | 2 | Pyridin-2-yl | 394 |
| 58 | 3,4-Cl₂—C₆H₃ | 2 | *(2-ethylsulfanyl-3-methylpyridine)* | 454 |
| 59 | 3,4-Cl₂—C₆H₃ | 2 | 4-OCH₃-quinoline-2-yl | 474 |
| 60 | 3,4-Cl₂—C₆H₃ | 2 | 4-OH-quinoline-4-yl | 460 |
| 61 | 3,4-Cl₂—C₆H₃ | 2 | *(2-allylsulfanyl-4-methylpyridine)* | 466 |
| 62 | 3,4-Cl₂—C₆H₃ | 2 | *(2-CN-5-methylpyridine)* | 410 |

US 7,304,077 B2

TABLE II-continued

| Compound No. | R¹ | n | R⁵ | M + H |
|---|---|---|---|---|
| 63 | 3,4-Cl₂—C₆H₃ | 2 | 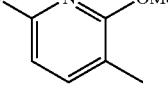 | 454 |
| 64 | 3,4-Cl₂—C₆H₃ | 2 | 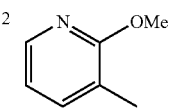 | 424 |
| 65 | 3,4-Cl₂—C₆H₃ | 2 | 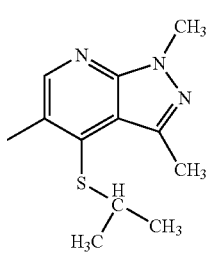 | 536 |
| 66 | 3,4-Cl₂—C₆H₃ | 2 | Isoquinoline-2-yl | 444 |
| 67 | 3,4-Cl₂—C₆H₃ | 2 | 6-CO₂CH₃-pyridin-2-yl | 452 |
| 68 | 3,4-Cl₂—C₆H₃ | 2 | 6-OCH₃-pyridin-3-yl | 424 |
| 69 | 3,4-Cl₂—C₆H₃ | 2 | 6-CH₃-pyridin-3-yl | 408 |
| 70 | 3,4-Cl₂—C₆H₃ | 2 | 2-OCH₂CF₃-pyridin-3-yl | 492 |
| 71 | 3,4-Cl₂—C₆H₃ | 2 | Quinoline-2-yl | 444 |
| 72 | 3,4-Cl₂—C₆H₃ | 2 | 2-Cl-6-CH₃-pyridin-4-yl | 442 |
| 73 | 3,4-Cl₂—C₆H₃ | 2 | 6-CH₃-pyridin-2-yl | 408 |
| 74 | 3,4-Cl₂—C₆H₃ | 2 | 8-OH-quinoline-2-yl | 460 |
| 75 | 3,4-Cl₂—C₆H₃ | 3 | quinoline-3-yl | 444 |
| 76 | 3,4-Cl₂—C₆H₃ | 2 | CH₂(3-F—C₆H₄) | 425 |
| 77 | 3,4-Cl₂—C₆H₃ | 2 | 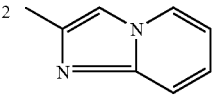 | 433 |
| 78 | 3,4-Cl₂—C₆H₃ | 3 | Isoquinoline-3-yl | 444 |
| 79 | 3,4-Cl₂—C₆H₃ | 2 | 4-(2-CH₃-pyridin-4-yl)-C₆H₄ | 484 |
| 80 | 3,4-Cl₂—C₆H₃ | 3 | [1,6]naphthyridine-2-yl | 445 |
| 81 | 3,4-Cl₂—C₆H₃ | 3 | 2-CH₃-[1,6]naphthyridine-3-yl | 459 |
| 82 | 3,4-Cl₂—C₆H₃ | 3 | 2-CH₃-quinoline-3-yl | 458 |
| 83 | 3,4-Cl₂—C₆H₃ | 2 | 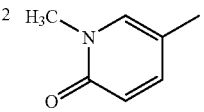 | 424 |
| 84 | 3,4-Cl₂—C₆H₃ | 2 | 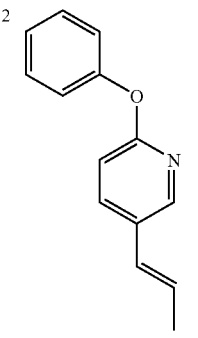 | 512 |

TABLE II-continued

| Compound No. | R¹ | n | R⁵ | M + H |
|---|---|---|---|---|
| 85 | 3,4-Cl₂—C₆H₃ | 2 | 1-ethyl-3,7-dimethyl-1,8-naphthyridin-4(1H)-one-yl | 503 |
| 86 | 3,4-Cl₂—C₆H₃ | 2 | quinolin-3-yloxymethyl | 474 |
| 87 | 3,4-Cl₂—C₆H₃ | 2 | 5-(trifluoromethyl)pyridin-2-ylthiomethyl | 508 |
| 88 | 3,4-Cl₂—C₆H₃ | 2 | 5-methyl-2-(pyridin-2-ylthiomethyl)furan-2-yl | 506 |
| 89 | 3,4-Cl₂—C₆H₃ | 2 | 1-(CH(CH₃)₂)-1H-1,2,3-benzotriazole-5-yl | 476 |
| 90 | 3,4-Cl₂—C₆H₃ | 2 | 2-CN-C₆H₄ | 418 |
| 91 | | | 3-nitro-2-(ethylthio)pyridin-... | 485 |
| 92 | 3,4-Cl₂—C₆H₃ | 2 | 5-(pyridin-2-yl)-2-thiophen-2-yl | 476 |
| 93 | 3,4-Cl₂—C₆H₃ | 2 | 2-(pyridin-2-yl)vinyl | 420 |

TABLE II-continued

| Compound No. | R¹ | n | R⁵ | M + H |
|---|---|---|---|---|
| 94 | 3,4-Cl₂—C₆H₃ | 2 | (5-(ethylthio)pyridin-3-yl)prop-1-enyl structure | 480 |
| 95 | 3,4-Cl₂—C₆H₃ | 2 | 1-(5-CF3-pyridin-2-yl)-piperidine-4-yl | 545 |
| 96 | 3,4-Cl₂—C₆H₃ | 2 | 4-((5-CF₃-pyridin-2-yl)oxy)phenyl structure | 554 |
| 97 | 3,4-Cl₂—C₆H₃ | 2 | 2,3,7-trimethylimidazo[1,2-a]pyridine structure | 461 |
| 98 | 3,4-Cl₂—C₆H₃ | 2 | 2-CF₃-[1,8]naphthyridin-3-yl | 513 |
| 99 | 3,4-Cl₂—C₆H₃ | 2 | 2-CF₃-[1,6]naphthyridin-3-yl | 513 |
| 100 | 3,4-Cl₂—C₆H₃ | 2 | CH₂-(5-(pyridin-2-yl)tetrazol-2-yl) structure | 476 |
| 101 | 3,4-Cl₂—C₆H₃ | 2 | 2-(ethylthio)-4-(pyridin-2-yl)pyrimidine structure | 518 |
| 102 | 3,4-Cl₂—C₆H₃ | 2 | CH₂(3-(pyridin-2-yl)-1H-pyrazol-1-yl) | 474 |

TABLE II-continued

| Compound No. | R¹ | n | R⁵ | M + H |
|---|---|---|---|---|
| 103 | 3,4-Cl₂—C₆H₃ | 2 | 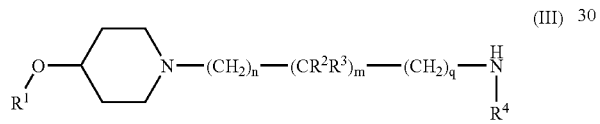 | 526 |
| 104 | 3,4-Cl₂—C₆H₃ | 2 | 6-CH₃-2-(SO₂CH₃)-pyridin-4-yl | 511 |

In a further aspect the present invention provides the a compound listed in Table II or a pharmaceutically acceptable salt thereof, or a solvate of a salt thereof. Where compounds of Table II can exist in different isomeric forms (such as enantiomers, diastereomers, geometric isomers or tautomers) the present invention covers all such isomers and mixtures thereof in all proportions. Suitable salts include acid addition salts such as a hydrochloride, dihydrochloride, hydrobromide, phosphate, acetate, diacetate, fumarate, maleate, tartrate, citrate, oxalate, methanesulphonate or p-toluenesulphonate.

The compounds of the invention can be prepared by reacting a compound of formula (III):

 (III)

with a compound of formula (IV):

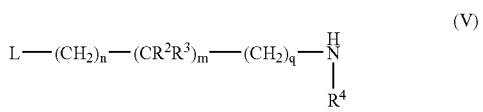 (IV)

wherein L is a leaving group (such as halogen). A compound of formula (III) can be prepared by reacting a compound of formula (V):

$$L-(CH_2)_n-(CR^2R^3)_m-(CH_2)_q-\overset{H}{\underset{R^4}{N}}$$ (V)

wherein L is a leaving group (such as halogen); with a compound of formula (VI):

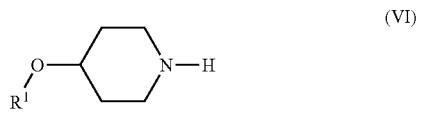 (VI)

Alternatively, compounds of the invention can be prepared by adapting the methods provided in the Examples below. Compounds of formula (III), (IV), (V) and (VI) can be prepared by using or adapting methods described in the art or by adapting the methods provided in the Examples below.

In another aspect the present invention provides processes for the preparation of the compounds of the invention.

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

The compounds of the invention are also H1 antagonists and may be used in the treatment of allergic disorders.

Examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, neplrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle.

According to a further feature of the invention there is provided a compound as hereinbefore defined or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity) in a warm blooded animal, such as man, in need of such treatment, which comprises administering to said animal an effective amount of a compound as hereinbefore defined or a pharmaceutically acceptable salt thereof or a solvate thereof.

According to another feature of the present invention there is provided a method for antagonising H1 in a warm blooded animal, such as man, in need of such treatment, which comprises administering to said animal an effective amount of a compound as hereinbefore defined or a pharmaceutically acceptable salt thereof or a solvate thereof.

The invention also provides a compound as hereinbefore defined or a pharmaceutically acceptable salt thereof or a solvate thereof, for use as a medicament.

In a further aspect the present invention provides the use of a compound as hereinbefore defined or a pharmaceutically acceptable salt thereof or a solvate thereof, in the manufacture of a medicament for use in therapy (for example modulating chemokine receptor activity (especially CCR3 receptor activity) or antagonising H1 in a warm blooded animal, such as man, or both).

The invention further provides the use of a compound as hereinbefore defined or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a warm blooded animal, such as man.

In a further aspect a compound of the invention, or a pharmaceutically acceptable salt thereof, is useful in the treatment of asthma {such as bronchial, allergic, intrinsic, extinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of the invention, or a pharmaceutically acceptable salt thereof, is useful in the treatment of asthma.

The present invention also provides the use of a compound of the invention, or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) or an H1 mediated disease state (such as an allergic disorder) in a warm blooded animal, such as man, which comprises administering to a mammal in need of such treatment an effective amount of a compound as hereinbefore defined or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition which comprises a compound as hereinbefore defined or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound as hereinbefore defined or a pharmaceutically-acceptable salt thereof (hereafter Compound X), for therapeutic or prophylactic use in humans:

(a)

| Tablet I | mg/tablet |
|---|---|
| Compound X | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1.0 |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limting Examples in which, unless stated otherwise:
(i) when given, $^1$H NMR data is quoted in the form of delta values for major diagnostic protons, given in parts per million (ppm) relative to tetramethylsilane (TMS) as an internal standard;
(ii) mass spectra (MS): generally only ions which indicate the parent mass are reported, and unless otherwise stated the mass ion quoted is the positive mass ion—(M+H)$^+$;
(iii) the title and sub-titled compounds of the examples and methods were named using the ACD/name program from Advanced Chemical Development Inc, Canada;
(iv) unless stated otherwise, reverse phase HPLC was conducted using a Symmetry, NovaPak or Ex-Terra reverse phase silica column;
(v) solvents were dried with MgSO$_4$ or Na$_2$SO$_4$;
(vi) unless otherwise stated reactions were performed at room temperature (RT); and,
(vii) the following abbreviations are used:

| | |
|---|---|
| THF | tetrahydrofuran; |
| DMF | N,N-dimethylformamide |
| DEAD | diethyl-azodicarboxylate |
| TFA | trifluoroacetic acid |
| PyBrop ® | Bromo-tris-pyrrolidino-phosphonium hexafluorophosphate |
| HPLC | High pressure liquid chromatography |

EXAMPLE 1

This Example illustrates the preparation of 4-(3,4-dichlorophenoxy)piperidine.

Step a: tert-Butyl 4-(3,4-dichlorophenoxy)-1-piperidinecarboxylate.

Diethyl azodicarboxylate (41.0 ml) was added to a solution of triphenylphosphine (62.9 g) in THF (800 ml) at 0° C. After 15 minutes 3,4-dichlorophenol (39.1 g) was added, after a further 15 minutes tert-butyl 4-hydroxy-1-piperidinecarboxylate (48.3 g) in THF (400 ml) was added dropwise over 30 minutes. The solution was stirred at room temperature for 16 hours and concentrated to a small volume. Purification by flash chromatography (ethyl acetate: isohexane 95:5) gave the sub-title compound as an oil (61.3 g).

MS: APCI (+ve): 246 (M-BOC+2H)

Step b: 4-(3,4-Dichlorophenoxy)piperidine

The product from Step (a) was dissolved in dichloromethane (600 ml) and trifluoroacetic acid (300 ml) was added. After 24 hours at room temperature the solution was evaporated and the resultant gum triturated under ether to give the sub-titled product as a solid (36.6 g). The free base was liberated by addition of aqueous NaOH (2M) and extraction with ethyl acetate followed by evaporation of solvent to give the title compound as a gum (25 g).

$^1$H NMR: (CDCl$_3$): δ 1.77 (1H, br s), 2.05–2.26 (4H, m), 3.20–3.49 (4H, m), 4.61 (1H, s), 6.69–7.52 (3H, m).

EXAMPLE 2

This Example illustrates the preparation of N-{3-[4-(3,4-dichlorophenoxy)-1-piperidinyl]propyl}-3-(methylsulfonyl)benzamide hydrochloride (a salt of Compound 20 of Table I).

Step a: tert-butyl 3-[4-(3,4-dichlorophenoxy)-1-piperidinyl]propylcarbamate

The product from Example 1 Step (b) (10 g) was dissolved in DMF (50 ml) and triethylamine (14.8 ml) was added. tert-Butyl 3-bromopropylcarbamate (10 g) was added and the solution stirred at room temperature for 24 hrs. The solvent was evaporated and the resulting solid was dissolved in ethyl acetate and water was added, the organic phase separated, dried with MgSO$_4$ and evaporated to a solid (17.51 g).

M: ESI (+ve): 403 (M+H)

Step b: 3-[4-(3,4-dichlorophenoxy)-1-piperidinyl]propylamine

The product from Step (a) (2 g) was dissolved in dioxane (100 ml) and 6N HCl (100 ml) added. After 18 hours at room temperature the solvent was evaporated and the resultant solid basified with NaOH (2N) to pH 11. The aqueous was extracted with ethyl acetate, the organic phase separated, dried with MgSO$_4$ and evaporated to leave the sub-title compound as an oil (1.1 g).

MS: ESI (+ve): 303 (M+H)

Step c: N-{3-[4-(3,4-dichlorophenoxy)-1-piperidinyl]propyl}-3-(methylsulfonyl)benzamide hydrochloride The product of Step (b) (0.15 g) was dissolved in DMF (4 ml). 3-Methylsulphonyl-benzoic acid (0.110 g), triethylamine (0.250 ml) and PyBrop® (0.350 g) were added. After 8 hours at room temperature the solvents were evaporated and the residue redissolved in ethyl acetate. The organics were washed with H$_2$O, dried with MgSO$_4$ and concentrated. Purification by reverse phase HPLC (with a gradient eluent system (25% MeCN/NH$_4$OAc$_{aq}$ (0.1%) to 95% MeCN//NH$_4$OAc$_{aq}$ (0.1%)) and formation of the hydrochloride salt by addition of HCl dissolved in ether and evaporation of solvent gave the title compound (0.145 g).

MS: APCI (+ve): 485 (M+H).

$^1$H NMR (400 MHz, DMSO): δ 1.93–2.08 (4H, m), 2.14–2.26 (2H, m), 3.11–3.20 (4H, m), 3.22 (3H, s), 3.33–3.39 (1H, m), 3.41 (2H, q), 3.50–3.57 (1H, m), 4.76–4.80 (1H, m), 7.02 (1H, dd), 7.25–7.32 (1H, m), 7.47–7.53 (1H, m), 7.74 (1H, t), 8.06 (1H, dt), 8.19 (1H, dt), 8.39 (1H, t), 8.74–8.80 (1H, m).

Melting point: 212° C.

EXAMPLE 3

This Example illustrates the preparation of N-{2-[4-(3,4-dichlorophenoxy)-1-piperidinyl]ethyl}-3-(methylsulfonyl)benzamide hydrochloride (a salt of Compound 19 of Table I).

Step a: tert-Butyl 2-[4-(3,4-dichlorophenoxy)-1-piperidinyl]ethylcarbamate

The product from Example 1 Step (b) (8.6 g) was dissolved in DMF (60 ml) and triethylamine (12 ml) was added. tert-Butyl 2-bromoethylcarbamate (7.8 g) was added and the solution stirred at room temperature for 12 hours. Diethyl ether/H$_2$O (1:1 500 ml) added and the organic phase separated, dried with MgSO$_4$ and evaporated to a gum. Purification by flash chromatography (dichloromethane: methanol: 880 NH$_3$ (aq) 98.5:1:0.5) gave the sub-title product (10 g).

MS: APCI (+ve): 389(M+H)

Step b: 2-[4-(3,4-dichlorophenoxy)-1-piperidinyl]ethylamine

The product from Step a (10 g) was dissolved in dichloromethane (200 ml) and trifluoroacetic acid (100 ml) added. After 12 hours at room temperature the solvent was evaporated and the resultant solid was washed with diethyl ether and filtered. The solid was redissolved in H$_2$O, basified with NaOH (2N) to pH 11. The aqueous was extracted with dichloromethane, the organic phase separated, dried and evaporated to leave the sub-title compound (3.5 g).

MS: APCI (+ve): 289 (M+H)

Step c: N-{2-[4-(3,4-dichlorophenoxy)-1-piperidinyl]ethyl}-3-(methylsulfonyl)benzamide hydrochloride The product of Step b (0.200 g) was dissolved in DMF (5 ml). 3-Methylsulphonyl-benzoic acid (0.132 g), triethylamine (0.250 ml) and PyBrop® (0.420 g) were added. After 24 hours at room temperature the solvents were evaporated and the residue redissolved in ethyl acetate. The organics were washed with H$_2$O, dried with MgSO$_4$ and concentrated. Purification by reverse phase HPLC (with a gradient eluent system (25% MeCN/NH$_4$OAc$_{aq}$ (0.1%) to 95% MeCN//NH$_4$OAc$_{aq}$ (0.1%)) (any excess NH$_4$OAc was removed by dissolving the compound in ethyl acetate and washing with aqueous saturated NaHCO$_3$ followed by drying of the organics with MgSO$_4$ and evaporation of solvent) and formation of the hydrochloride salt by addition of HCl dissolved in ether and evaporation of solvent gave the title compound (0.084 g).

MS: APCI (+ve): 471 (M+H)

$^1$H NMR: (399.979 MHz, D$_2$O) δ 2.09–2.19 (2H, m), 2.25–2.33 (2H, m), 3.30 (3H, s), 3.38–3.46 (2H, m), 3.48 (2H, t), 3.58–3.66 (2H, m), 3.80–3.91 (3H, m), 6.98 (1H, dd), 7.25 (1H, d), 7.47 (1H, d), 7.82 (1H, t), 8.17 (2H, t), 8.36 (1H, s).

Melting point: 219° C.

EXAMPLE 4

This Example illustrates the preparation of N-{2-[4-(3,4-dichlorophenoxy)-1-piperidinyl]ethyl}-3-[(methylsulfonyl)methyl]benzamide (Compound 5 of Table I).

The product of Example 3, Step (b) (0.200 g) was dissolved in dichloromethane (4 ml). 3-[(Methylsulfonyl)methyl]benzoic acid (see WO00/15609; or by hydrolysis of methyl 3-[(methylsulfonyl)methyl]benzoate which is commercially available; 0.132 g), triethylamine (0.289 ml) and PyBrop® (0.483 g) were added. After 24 hours at room temperature NaHCO$_3$(aq) was added and product extracted with diethyl ether. The organics were dried with MgSO$_4$ and concentrated. Purification by reverse phase HPLC (with a gradient eluent system (25% MeCN/NH$_4$OAc$_{aq}$ (0.1%) to 95% MeCN/NH$_4$OAc$_{aq}$ (0.1%)) (any excess NH$_4$OAc was removed by dissolving the compound in dichloromethane and washing with aqueous saturated NaHCO$_3$ followed by drying of the organics with MgSO$_4$ and evaporation of solvent) gave the title compound (0.101 g).

MS: APCI(+ve): 485 (M+H).

$^1$H NMR (299.946 MHz, DMSO) δ 1.58–1.67 (2H, m), 1.89–1.97 (2H, m), 2.27–2.35 (2H, m), 2.49–2.53 (2H, m), 2.70–2.79 (2H, m), 2.94 (3H, s), 3.38–3.43 (2H, m), 4.41–4.49 (1H, m), 4.54 (2H, s), 4.81–4.83 (1H, m) 6.96–7.00 (1H, m), 7.25–7.27 (1H, m), 7.47–7.57 (3H, m), 7.82–7.87 (2H, m), 8.42–8.47 (1H, m).

Melting point: 112–114° C.

EXAMPLE 5

This Example illustrates the preparation of N-{2-[4-(3,4-dichlorophenoxy)-1-piperidinyl]ethyl}-4-[(methylsulfonyl)methyl]benzamide (Compound 7 of Table I).

Prepared in a similar manner to the method of Example 4 using 4-[(methylsulfonyl)methyl]benzoic acid (J. Med. Chem. (1997), 40(25), 4030–4052) to give the title compound as a solid (0.160 g).

MS: APCI(+ve): 485 (M+H)

$^1$H NMR (299.946 MHz, DMSO) δ 1.56–1.65 (2H, m), 1.89–1.98 (2H, m), 2.26–2.35 (2H, m), 2.65–2.82 (2H, m), 2.71–2.78 (2H, m), 2.92 (3H, s), 3.37–3.41 (2H, m), 4.40–4.49 (1H, m), 4.56 (2H, s), 6.96–7.00 (1H, m), 7.24–7.27 (1H, m), 7.48–7.53 (3H, m), 7.82–7.86 (2H, m), 8.42–8.47 (1H, m).

Melting point: 179–181° C.

EXAMPLE 6

This Example illustrates the preparation of N-(cyclopropylmethyl)-N-{2-[4-(3,4-difluorophenoxy)-1-piperidinyl]ethyl}-4-fluoro-3-methoxybenzamide (Compound 15 of Table I).

Step a: tert-Butyl 4-(3,4-difluorophenoxy)-1-piperidinecarboxylate

The sub-title compound was prepared according to the method of Example 1, Step a using 3,4-difluorophenol to afford an oil (5.4 g).

MS: ESI (+ve): 213 (M-BOC+H)

Step b: 4-(3,4-Difluorophenoxy)piperidine

The sub-title compound was prepared according to the method of Example 1, Step b to afford a pale yellow oil (3 g).

MS: ESI (+ve): 214 (M+H)

Step c: tert-butyl 2-[4-(3,4-difluorophenoxy)-1-piperidinyl]ethylcarbamate

The product of Step b (5 g) was dissolved in DMF (27 ml) and triethylamine (7.7 ml) was added. tert-Butyl 2-bromoethylcarbamate (5.8 g) was added and the solution stirred at room temperature for 24 hrs. The solvent was evaporated and the residue dissolved in ethyl acetate and washed with water. The organic phase separated, dried and evaporated. Purification by flash chromatography (dichloromethane:methanol 97:3) gave the sub-title product as an oil (10 g) containing a small amount of DMF.

MS: APCI(+ve): 357 (M+H)

Step d: 2-[4-(3,4-Difluorophenoxy)-1-piperidinyl]ethylamine

The product of Step c (10 g) was dissolved in dioxane (114 ml) and HCl (6N) (114 ml) was added and the reaction stirred for 2 hours. Organic solvent was evaporated and aqueous NaOH (2M) added. The product was extracted with ethyl acetate, the combined organic extracts dried with Na$_2$SO$_4$ and concentrated to give the sub-title product as an oil (4.65 g).

$^1$H NMR: (400 MHz, CDCl$_3$) δ 1.74–1.83 (2H, m), 1.95–2.00 (2H, m), 2.26–2.31 (2H, m), 2.43 (2H, t), 2.73 (2H, br s), 2.79 (2H, t), 4.17–4.23 (1H, m), 6.58–7.07 (3H, m).

MS: APCI(+ve): 257 (M+H)

Step e: N-(Cyclopropylmethyl)-N-{2-[4-(3,4-difluorophenoxy)-1-piperidinyl]ethyl}amine The product of Step d (0.4 g) dissolved in MeOH (6 ml) was added to cyclopropanecarbaldehyde (0.116 ml) and the resulting mixture was stirred for 4 hours. The solvent was evaporated, the residue re-dissolved in methanol (6 ml) and NaBH$_4$ (0.095 g) added and the mixture left for 30 minutes. Aqueous sodium hydroxide (1N) was added and the aqueous extracted with diethyl ether. The organic extracts were dried with Na$_2$SO$_4$, filtered and concentrated to give the sub-title product as an oil (0.493 g).

MS: APCI(+ve): 311 (M+H)

Step f: N-(Cyclopropylmethyl)-N-{2-[4-(3,4-difluorophenoxy)-1-piperidinyl]ethyl}-4-fluoro-3-methoxybenzamide To a solution of 4-fluoro-3-methoxybenzoic acid (0.082 g) in THF (1 ml) was added carbonyldiimidazole (0.078 g) and the resulting solution stirred at room temperature for 10 minutes before addition of the product of Step e (0.15 g) in THF (1.5 ml). The mixture was stirred for 2 hours and the solvent removed by evaporation to yield a colourless gum. Purification by reverse phase HPLC (with a gradient eluent system 25% MeCN/NH$_4$OAc(aq) (0.1%) to 95% MeCN// NH$_4$OAc(aq) (0.1%)) gave the title compound (0.011 g).

MS: ESI(+ve) 463(M+H)

$^1$H NMR (300 MHz, CDCl$_3$) δ 0.13–0.22 (2H, m), 0.52–0.58 (2H, m), 0.93–1.04 (1H, m), 1.70–1.81 (2H, m), 1.88–1.99 (2H, m), 2.25–2.40 (2H, m), 2.55–2.79 (4H, m), 3.22–3.33 (2H, m), 3.59–3.71 (2H, m), 3.90 (3H, s), 4.14–4.22 (1H, m), 6.55–6.61 (1H, m), 6.70 (1H, ddd), 6.92 (1H, ddd), 7.01–7.06 (2H, m), 7.08 (1H, d).

EXAMPLE 7

This Example illustrates the preparation of N-{2-[4-(3,4-difluorophenoxy)-1-piperidinyl]ethyl}-3-(methylsulfonyl) benzamide hydrochloride (a salt of Compound 16 of Table I).

The product of Example 6, Step d (0.200 g) was dissolved in THF (4 ml), 3-methylsulphonylbenzoic acid (0.156 g, N,N-di-isopropylethylamine (0.407 ml) and PyBrop® (0.401 g) were added. After 18 hours at room temperature ethyl acetate and aqueous NaHCO$_3$ solution were added. The product was extracted with ethyl acetate, the combined organic extracts dried with MgSO$_4$ and concentrated. Purification by reverse phase HPLC (with a gradient eluent system 45% MeCN/NH$_4$OAc$_{aq}$ (0.1%) to 95% MeCN// NH$_4$OAc$_{aq}$ (0.1%)) and formation of the hydrochloride salt by addition of HCl dissolved in ether and evaporation of solvent gave the title compound (0.205 g).

MS: APCI(+ve) 439 (M+H)

$^1$H NMR (300 MHz, DMSO) δ 1.93–2.26 (4H, m), 3.05–3.76 (10H, m), 4.50–4.60 (1H, m), 4.76 (1H, brs), 6.81–8.50 (7H, m), 9.29–9.33 (1H, m), 10.81 (1H, br s).

EXAMPLE 8

This Example illustrates the preparation of N-{3-[4-(3,4-dichlorophenoxy)-1-piperidinyl]propyl}-2-(2,5-dihydro-1H-pyrrol-1-yl)-1,3-benzothiazole-6-carboxamide (Compound 17 of Table I).

Prepared in a similar manner to the method of Example 6, Step f using the product of Example 2, Step b and 2-(2,5-dihydro-1H-pyrrol-1-yl)-1,3-benzothiazole-6-carboxylic acid to give the title compound as a solid (0.026 g).

MS: ESI(+ve) 531 (M+H)

$^1$H NMR: (399.978 MHz, CDCl$_3$) δ 1.66–2.25 (6H, m), 2.11–2.24 (2H, m), 2.72–2.83 (3H, m), 2.85–2.95 (2H, m), 3.64 (2H, q), 4.37-.4.45 (1H, m), 6.41 (2H, t), 6.75 (1H, dd), 7.00 (1H, d), 7.21 (2H, d), 7.47 (2H, t), 7.89 (1H, d), 7.94–7.96 (1H, m), 8.39 (1H, s), 8.42–8.47 (1H, m).

EXAMPLE 9

This Example illustrates the preparation of N-{2-[4-(3,4-difluorophenoxy)-1-piperidinyl]ethyl}-3-methoxy-N-methylbenzamide hydrochloride (Compound 18 of Table I).

Step a: N-{2-[4-(3,4-Difluorophenoxy)-1-piperidinyl]ethyl}-2,2,2-trifluoroacetamide To a solution of the product of Example 6, Step d (1.5 g) and triethylamine (2.45 ml) at 0° C. in dichloromethane (20 ml) was added trifluoroacetic anhydride (1.24 ml) dropwise over 10 minutes. After warming to RT the reaction mixture was partitioned between water (20 ml) and dichloromethane (20 ml). The organic phase was separated and dried with MgSO$_4$. Purification by flash chromatography (dichloromethane:methanol: 98:2)gave the sub-title compound as a colourless oil (1.64 g).

MS: ESI(+ve) 353(M+H)

$^1$H NMR: (299.944 MHz, CDCl$_3$) δ1.75–1.86 (2H, m), 1.93–2.02 (2H, m), 2.36 (2H, ddd), 2.58 (2H, t), 2.73 (2H, td), 3.44 (2H, q), 4.25 (1H, m), 6.57–6.63 (1H, m), 6.72 (1H, ddd), 6.96–7.07 (1H, m), 7.05 (1H, q).

Step b: N-{2-[4-(3,4Difluorophenoxy)-1-piperidinyl]ethyl}-2,2,2-trifluoro-N-methylacetamide A solution of the product of Step a (1.64 g) in THF (5 ml) was added dropwise to a suspension of sodium hydride (0.205 g 60% suspension in oil) in THF (20 ml) at 0° C. The reaction mixture was allowed to warm to RT over 30 min before cooling again to 0° C. Methyl iodide (0.29 ml) in THF (5 ml) was added dropwise. The reaction mixture was left string at RT for 18 hours before removal of solvents by evaporation. Purification by flash chromatography (dichloromethane:methanol: 880 NH$_3$ (aq) 98.5:1:0.5) gave the title product (0.3 g).

MS: ESI(+ve) 367(M+H)

Step c: N-{2-[4-(3,4-Difluorophenoxy)-1-piperidinyl]ethyl}-N-methylamine

To a solution of the product of Step b (0.3 g) in ethanol (15 ml) was added a 2M solution of sodium hydroxide (5 ml). The mixture was stirred at RT for 72 hours. The resultant mixture was partitioned between EtOAc (20 ml) and water (20 ml). The organic layer was separated and dried with MgSO$_4$. Removal of solvent under reduced pressure gave the title compound (0.2 g).

MS: ESI(+ve) 367(M+H)

$^1$H NMR (300 MHz, CDCl$_3$) δ 1.74–1.84 (2H, m), 1.92–2.01 (2H, m), 2.25–2.33 (2H, m), 2.46 (3H, s), 2.51 (2H, t), 2.68–2.77 (2H, m), 2.68 (2H, t), 4.20 (1H, tt), 6.57–6.62 (1H, m), 6.72 (1H, ddd), 7.04 (1H, dt).

Step d: N-{2-[4-(3,4-difluorophenoxy)-1-piperidinyl]ethyl}-3-methoxy-N-methylbenzamide hydrochloride To a solution of the product of Step c (0.145 g) and triethylamine (0.224 ml) in THF (3 ml) at 0° C. was added a solution 3-methoxybenzoyl chloride (0.083 ml) in THF (2 ml). The mixture was stirred for 1 hour then partitioned between ethyl acetate and water. The organic layer was separated and dried with MgSO$_4$ and the solvent removed by evaporation. Purification by reverse phase HPLC (with a gradient eluent system 25% MeCN/NH$_4$OAc(aq) (0.1%) to 95% MeCN//NH$_4$OAc(aq) (0.1%)) evaporation of solvent and the residue was dissolved in diethyl ether and HCl (1 ml 1M solution in diethyl ether) added. Filtration gave the title compound (0.137 g).

MS: ESI(+ve) 405(M+H)

$^1$H NMR (400 MHz, D$_2$O) δ 1.91–2.02 (1H, m), 2.13 (1H, t), 2.30 (1H, d), 2.44 (1H, d), 3.06 (3H, s), 3.24 (1H, t), 3.35–3.47 (2H, m), 3.52 (2H, t), 3.65 (1H, d), 3.80 (1H, t), 3.86 (3H, s), 3.97 (2H, t), 6.77–6.85 (1H, m), 6.94–7.16 (4H, m), 7.20–7.27 (1H, m), 7.45–7.52 (1H, m)

Melting point: 218° C.

EXAMPLE 10

This Example illustrates the preparation of N-{2-[4-(3,4-dichlorophenoxy)-1-piperidinyl]ethyl}-3-hydroxybenzamide (Compound 8 of Table II).

Step a: N-{2-[4(3,4-dichlorophenoxy)-1-piperidinyl]ethyl}-3-methoxybenzamide

The product from Example 3, Step b (2.00 g) was dissolved in TBF (100 ml) and triethylamine (2.10 g) added. The solution was then cooled with stirring to 0° C. and to it 3-methoxybenzoyl chloride was added dropwise as a solution in THF (10 ml). Reaction was left to warm to room temp and left for 24 hours then water was added and the organics extracted into ethyl acetate. The combined organics were dried with MgSO$_4$ and the solvent removed by evaporation. The crude product was purified by flash chromatography to leave the sub-title product as a pale yellow oil (1.38 g).

MS: APCI(+ve): 424 (M+H)

Step b: N-{2-[4-(3,4-dichlorophenoxy)-1-piperidinyl]ethyl}-3-hydroxybenzamide

The product from Step a (1.3 g) was dissolved in dichloromethane (40 ml) under nitrogen and cooled to −78° C. Boron tribromide was then added slowly and reaction left to warm to room temp and left over 72 hours. Methanol was added followed by flash silica (for preabsorption) and purification by flash chromatography (dichloromethane:methanol: 880 NH$_3$ (aq) 96.8:4:0.2) to give the title product (1.1 g).

$^1$H NMR (300 MHz, CDCl$_3$) δ 1.80–1.91 (2H, m), 1.97–2.09 (2H, m), 2.48 (2H, t), 2.69 (2H, t), 2.80 (2H, t), 3.60 (2H, q), 4.33 (1H, quintet), 6.75 (1H, dd), 6.91 (1H, ddd), 7.00 (1H, d), 7.16 (1H, d), 7.21 (1H, d), 7.31 (1H, d), 7.40 (1H, t).

EXAMPLE 11

The present Example illustrates the preparation of N-{2-[4-(3,4-dichlorophenoxy)1-piperidinyl]ethyl}-3-[2-(dimethylamino)-2-oxoethoxy]benzamide acetate (a salt of Compound 86 of Table II).

The product from Example 10, Step b (0.150 g) was dissolved with 2-chloro-N,N-dimethylacetamide (0.045 g) in dimethylformamide (10 ml) with stirring under nitrogen. Caesium carbonate (0.241 g) was then added and reaction left for 24 hours. Evaporation of solvent and purification by flash chromatography (dichloromethane:methanol: 880 NH$_3$ (aq) 96.9:3:0.15) followed by reverse phase HPLC (with a gradient eluent system (25% MeCN/NH$_4$OAc$_{aq}$ (0.1%) to 95% MeCN//NH$_4$OAc$_{aq}$ (0.1%)) gave the product as an acetate salt (0.090 g).

MS: APCI(+ve): 494 (M+H)

¹H NMR: (299.944 MHz, CDCl₃) δ 1.74–1.88 (2H, m), 1.96–2.06 (2H, m), 2.17 (3H, s), 2.38–2.47 (2H, m), 2.65 (2H, t), 2.73–2.85 (1H, m), 2.99 (3H, s), 3.08 (3H, s), 3.56 (2H, q), 3.98–4.13 (1H, m), 4.27–4.37 (1H, m), 4.75 (2H,.s), 6.76 (1H, dd), 6.99–7.04 (2H, m), 7.08–7.12 (1H, m), 7.28–7.41 (4H, m).

EXAMPLE 12

This Example illustrates the preparation of methyl{3-[({2-[4-(3,4-dichlorophenoxy)-1-piperidinyl]ethyl}amino) carbonyl]phenoxy}acetate hydrochloride (a salt of Compound 87 of Table II).

To a solution of the product from Example 10, Step b (0.250 g) and methyl chloroacetate (0.066 g) in dimethylformamide (10 ml) under nitrogen was added caesium carbonate (0.4 g). The reaction was left to stir for 24 hours. Water was added and organics extracted into ethyl acetate and dried with MgSO₄. Evaporation of solvent and purification by reverse phase HPLC (with a gradient eluent system 25% MeCN/NH₄OAc$_{aq}$ (0.1%) to 95% MeCN//NH₄OAc$_{aq}$ (0.1%)) gave the product. The isolated product was then converted to title product by dissolving in diethylether, adding ethereal hydrochloric acid and triturating from diethylether to give the titled product as a white powder (0.050 g).

MS: APCI(+ve): 481 (M+H)

¹H NMR (300 MHz, D₂O) δ 1.94–2.02 (2H, m), 2.38–2.46 (2H, m), 3.25 (2H, t), 3.41–3.44 (2H, m), 3.48 (2H, t), 3.56–3.66 (2H, m), 3.84 (3H, s), 4.61–4.74 (1H, m), 4.88 (2H, s), 6.99 (1H, dd), 7.21–7.27 (2H, m), 7.37–7.40 (2H, m), 7.49 (2H, t).

EXAMPLE 13

This Example illustrates the preparation of N-{2-[4-(3,4-dichlorophenoxy)-1-piperidinyl]ethyl}-3-(2-hydroxyethoxy)benzamide hydrochloride (a salt of Compound 21 of Table I).

To a solution of the product from Example 10, Step b (0.2 g) and 2-(2-bromoethoxy)tetrahydro-2H-pyran (0.209 g) in dimethylformamide (10 ml) under nitrogen was added caesium carbonate (0.326 g). After stirring for 24 hours, water was added and organics extracted into ethyl acetate separated and dried with MgSO₄. Evaporation of solvent and purification by flash chromatography (eluent 2% MeOH, 0.1% 0.880 ammonia, 97.9% dichloromethane) gave the THP protected titled product. Deprotection of the product was achieved by stirring in trifluoroacetic acid:dichloromethane (1:2) solution (65 ml) for 30 mins. NaHCO₃(aq) was added. The product was extracted with ethyl acetate, the combined organic extracts dried with MgSO₄ and concentrated to give the crude titled product. Purification by reverse phase HPLC (with a gradient eluent system 25% MeCN/NH₄OAc$_{aq}$ (0.1%) to 95% MeCN//NH₄OAc$_{aq}$ (0.1%)) was achieved. The isolated product was then converted to title product by dissolving in diethylether, adding ethereal hydrochloric acid and triturating from diethylether to give the titled product (0.069 g).

MS: APCI(+ve): 453 (M+H)

¹H NMR (400 MHz, DMSO) δ 2.01–2.15 (2H, m), 2.27–2.34 (2H, m), 3.20–3.26 (2H, m), 3.32–3.41 (2H, m), 3.49–3.57 (2H, m), 3.69–3.90 (4H, m), 4.11 (2H,t), 4.60–4.75 (1H, m), 7.05–7.12 (1H, m), 7.17 (1H,d), 7.41–7.47 (2H, m), 7.54–7.64 (2H, m) 8.96 (1H, s).

EXAMPLE 14

This Example illustrates the preparation of N-{2-[4-(3,4-dichlorophenoxy)-1-piperidinyl]ethyl}-3-[(2-hydroxyethyl) sulfonyl]benzamide acetate (a salt of Compound 22 of Table I).

Step a: 3-{[2-(tetrahydro-2H-pyran-2-yloxy)ethyl] sulfonyl}benzoic acid

To a solution of 3-sulfino-benzoic acid (1 g) and 2-iodoethyl tetrahydro-2H-pyran-2-yl ether (1.4 g) in water (20 ml) and ethanol (20 ml) was added NaOH solution to give a pH of 9. The resulting mixture was refluxed for 3 hours before evaporation of the ethanol. The aqueous was acidified to pH3 and the product extracted with EtOAc. The organic layer was separated, dried with MgSO₄ and solvent removed by evaporation to give the sub-title compound (0.25 g).

MS: ESI(+ve) 230(M+H−THP)

Step b: N-{2-[4-(3,4-dichlorophenoxy)-1-piperidinyl] ethyl}-3-[(2-hydroxyethyl)-sulfonyl]benzamide acetate To a solution of the product of Step a (0.20 g), the product of Example 3, Step b (0.25 g) and diisopropylethyl amine (0.33 ml) in dichloromethane (5 ml) was added PyBrOP® (0.37 g) and the mixture stirred for 24 hours. Purification by Biotage® 40M eluting 20% MeCN/2% 880 ammonia/78% dichloromethane gave a colourless oil (0.49 g) which was dissolved in trifluoroacetic acid (9 ml) and water (1 ml) and stirred for 15 minutes. The solvents were evaporated under reduced pressure and purification by reverse phase HPLC (with a gradient eluent system 25% MeCN/NH₄OAcaq (0.1%) to 95% MeCN//NH₄OAc(aq) (0.1%)) (any excess NH₄OAc was removed by dissolving the compound in ethyl acetate and washing with aqueous saturated NaHCO₃ followed by drying of the organics with MgSO₄ and evaporation of solvent) and formation of the acetate salt by dissolving in acetic acid and evaporation of the excess acid gave the title product (0.050 g).

MS: ESI(+ve) 501 (M+H)

¹H NM (400 MHz, CDCl₃) δ 1.79–1.87 (2H, m), 1.95–2.04 (3H, m), 2.42 (2H, t), 2.65 (2H, t), 2.77 (2H, t), 3.43 (2H, t), 3.58 (2H, q), 3.80 (2H, t), 4.29–4.35 (1H, m), 6.76 (1H, dd), 6.92–6.97 (1H, m), 7.00 (1H, d), 7.31 (1H, d), 7.65 (1H, t), 8.05 (1H, d), 8.10 (1H, d), 8.30 (1H, t)

EXAMPLE 15

This Example illustrates the preparation of N-{2-[4-(3,4dichlorophenoxy)-1-piperidinyl]ethyl}-3-[(methylamino) sulfonyl]benzamide acetate (a salt of Compound 9 of Table I).

Prepared in a similar manner to the method of Example 14, Step b using the product from Example 3, Step b and 3-[(methylamino)sulfonyl]benzoic acid to give the title product (0.269 g).

MS: ESI(+ve) 486 (M+H)

¹H NM (500.076 MHz, DMSO) δ 1.57–1.65 (2H, m), 1.91–1.96 (2H, m), 2.31 (2H, t), 2.43(3H, s), 2.49–2.52 (5H, m), 2.72–2.78 (2H, m), 3.41 (2H, q), 4.45 (1H, m), 6.99 (1H, dd), 7.26 (1H, d), 7.50 (1H, d), 7.52–7.58 (1H, m), 7.72 (1H, t), 7.91 (1H, d), 8.09 (1H, d), 8.24(1H, s), 8.69 (1H, t).

EXAMPLE 16

This Example illustrates the preparation of N-{2-[4-(3,4-dichlorophenoxy)-1-piperidinyl]ethyl}-3-(2-methoxyethoxy)benzamide hydrochloride (A salt of Compound 12 of Table I).

Prepared in a similar manner to the method of Example 14, Step b using the product from Example 3, Step b and 3-(2-methoxyethoxy)benzoic acid to give the title product after formation of a hydrochloride salt (0.213 g).

MS: ESI(+ve) 467 (M+H)

¹H NMR: (500.076 MHz, DMSO) δ 1.83–1.91 (1H, m), 2.02–2.14 (2H, m), 2.22–2.31 (1H, m), 3.07–3.16 (2H, m), 3.17–3.25 (2H, m), 3.32 (3H, s), 3.44–3.52 (1H, m), 3.62–3.73 (2H, m), 3.68 (2H, t), 4.15 (2H, t), 4.57–4.65 (1H, m), 4.81–4.85 (1H, m), 7.02–7.09 (1H, m), 7.14 (1H, d), 7.35–7.38 (1H, m), 7.40 (1H, t), 7.45–7.49 (2H, m), 7.56 (1H, t), 8.78–8.85 (1H, m).

EXAMPLE 17

This Example illustrates the preparation of tert-butyl 2-{3-[({2-[4-(3,4-dichlorophenoxy)-1-piperidinyl]ethyl}amino)carbonyl]phenoxy}ethylcarbamate acetate (a salt of Compound 23 of Table I).

Step a: Methyl 3-{2-[(tert-butoxycarbonyl)amino]ethoxy}benzoate

To a solution of tert-butyl 2-bromoethylcarbamate (5 g) and methyl 3-hydroxybenzoate (3.4 g) in dimethylformamide (60 ml) was added caesium carbonate (14.5 g) and the reaction stirred for 12 hours before partitioning between water and ethyl acetate. The organic layer was separated, dried with $MgSO_4$ and the solvent removed by evaporation. Purification by flash chromatography (ethyl acetate:isohexane 92.5:7.5) gave the sub-title product as a colourless oil (3 g).

$^1$H NMR ($CDCl_3$) δ 1.41 (9H, s), 3.51 (2H, q), 3.87 (3H, s), 4.02 (2H, t), 5.03–5.10 (1H, m), 7.05 (1H, ddd), 7.30 (1H, t), 7.50–7.51 (1H, m), 7.60 (1H, dt).

Step b: 3-{2-[(tert-butoxycarbonyl)amino]ethoxy}benzoic acid

To a solution of the product of Step a (6 g) in THF (120 ml) was added lithium hydroxide monohydrate (4.9 g) and enough water to ensure fall disolution. The reaction was stirred for 12 hours, acidified with 2M HCl and partitioned between ethyl acetate and water. The organic layer was separated, dried with $MgSO_4$ and the solvent removed by evaporation to give the title compound (3.9 g).

$^1$H NMR (400 MHz, DMSO) δ 1.38 (9H, s), 3.31 (2H, t), 4.01 (2H, t), 7.02 (1H, t), 7.19 (1H, dt), 7.39–7.43 (2H, m), 7.53 (1H, d), 12.97 (1H, s).

Step c: tert-butyl 2-{3-[({2-[4-(3,4-dichlorophenoxy)-1-piperidinyl]ethyl}amino)-carbonyl]phenoxy}ethylcarbamate acetate Prepared in a similar manner to the method of Example 14, Step b using the product from Step b and the product of Example 3, Step b to give the title product (0.234 g).

MS: ESI(+ve) 552 (M+H)

$^1$H NMR: (500.076 MHz, DMSO) δ 1.38 (9H, s), 1.57–1.64 (2H, m), 1.89–1.94 (2H, m), 1.96 (3H, s), 2.29 (2H, t), 2.47–2.51 (6H, m), 2.72–2.76 (2H, m), 4.00 (2H, t), 4.43–4.46 (1H, m), 6.98 (1H, dd), 7.02 (1H, t), 7.07–7.09 (1H, m), 7.26 (1H, d), 7.35–7.43 (3H, m), 7.50 (1H, d), 8.39 (1H, t).

EXAMPLE 18

This Example illustrates the preparation of N-{2-[4(3,4-dichlorophenoxy)-1-piperidinyl]ethyl}-3-[(methylsulfonyl)amino]benzamide (Compound 24 of Table I).

Step a: 3-amino-N-{2-[4-(3,4-dichlorophenoxy)-1-piperidinyl]ethyl}benzamide

Prepared in a similar manner to the method of Example 14, Step b using the product from Example 3, Step b and 3-aminobenzoic acid to give the sub-title product (0.183 g).

MS: ESI(+ve) 448 (M+H).

Step b: N-{2-[4-(3,4-dichlorophenoxy)-1-piperidinyl]ethyl}-3-[(methylsulfonyl)amino]-benzamide To a solution of the product of Step a in pyridine (2 ml) was added methanesulfonyl chloride (0.034 ml) and the reaction left to stir for 5 mins. Water (0.5 ml) was added and the solvents evaporated. Purification by reverse phase HPLC (with a gradient eluent system (25% MeCN/$NH_4OAc_{aq}$ (0.1%) to 95% MeCN//$NH_4OAc_{aq}$ (0.1%)) (any excess $NH_4OAc$ was removed by dissolving the compound in dichloromethane and washing with aqueous saturated $NaHCO_3$ followed by drying of the organics with $MgSO_4$ and evaporation of solvent) gave the title product (0.091 g).

MS: APCI (+ve) 486 (M+H)

$^1$H NMR (400 MHz, $CDCl_3$) δ 1.80–1.87 (2H, m), 1.96–2.04 (2H, m), 2.38–2.43 (2H, m), 2.64–2.67 (2H, m), 2.79–2.84 (2H, m), 3.02 (3H, s), 3.57–3.62 (2H, m), 4.31–4.32 (1H, m), 6.75–7.90 (9H, m).

Melting point: 150–151° C.

EXAMPLE 19

This Example illustrates the preparation of 3-(2-aminoethoxy)-N-{2-[4-(3,4-dichlorophenoxy)-1-piperidinyl]ethyl}benzamide dihydrochloride (a salt of Compound 25 of Table I).

To a solution of the product of Example 17, Step c (0.163) in dioxane (5 ml) was added concentrated HCl (1 ml) and the mixture stirred for 3 hours. The solvents were evaporated and excess HCl removed by azeotroping with toluene. The residue was dissolved in water and after freeze drying gave the title compound (0.145 g).

MS: ESI(+ve) 452 (M+H).

$^1$H NMR (300 MHz, DMSO) δ 1.96–2.10 (2H, m), 2.18–2.30 (2H, m), 3.06–3.35 (6H, m), 3.42–3.50 (1H, m), 3.65–3.83 (3H, m), 4.28 (2H, t), 4.58–4.70 (1H, m), 4.85 (1H, s), 7.02–7.18 (2H, m), 7.33–7.45 (2H, m), 7.50–7.62 (3H, m), 8.33 (2H, s), 9.04–9.11 (1H, m).

EXAMPLE 20

This Example illustrates the preparation of derivatives of (1S)-2-[4-(3,4-difluorophenoxy)-1-piperidinyl]-1-phenylethylamine Step a: tert-butyl (1S)-2-[4-(3,4-difluorophenoxy)-1-piperidinyl]-2-oxo-1-phenylethylcarbamate To (2S)-[(tert-butoxycarbonyl)amino](phenyl)ethanoic acid (1 g) in $CH_2Cl_2$/DMF (1:1) (20 ml) was added 1-ethyl-3-[3-(dimethylamino)-propyl]carbodiimide hydrochloride (0.989 g) and left to stir for 5 mins. The product of example 6, step b (0.848 g) was then added and the reaction left to stir for 24 hrs. Aqueous $NaHCO_3$ solution was added and the product extracted with $CH_2Cl_2$. The organic phase was washed with $H_2O$ dried with $Na_2SO_4$ and purification by flash chromatography (ethyl acetate:isohexane 30:70) gave the sub-title compound (0.650 g).

MS: ESI(+ve): 447 (M+H)

Step b: (1S)-2-[4-(3,4-difluorophenoxy)-1-piperidinyl]-2-oxo-1-phenylethylamine

The product from Example 20, step a (0.650 g) was dissolved in dichloromethane (7 ml) and trifluoroacetic acid (2 ml) was added. After 3 hr at room temperature the solution was evaporated and aqueous NaOH (2M) added. The product was extracted with ethyl acetate, the combined organic extracts dried with $Na_2SO_4$ and concentrated to give the sub-title product as an oil (0.544 g).

MS: ESI(+ve): 347 (M+H)

Step c: (1S)-2-[4-(3,4-difluorophenoxy)-1-piperidinyl]-1-phenylethylamine

The product from Example 20, step b) (0.544 g) was dissolved in THF (5 ml) and borane [10.05 ml (1M in THF)] was added. The reaction was heated at reflux for 2 hours. The reaction was quenched slowly with MeOH and the solvents evaporated. Aqueous HCl (5 ml Concentrated HCl:

5 ml H₂O) was added and the reaction heated at 70° C. for 1 hour. NaOH (2M) was added until pH 9 was reached. The product was extracted with CH₂Cl₂ and the combined organics washed with saturated aqueous NaHCO₃, dried with Na₂SO₄ and solvents evaporated. Purification by flash chromatography (dichloromethane:methanol: 880 NH₃ (aq) 89:10:1)gave the sub-title compound as an oil (0.377 g).

¹H NMR: (300 MHz, CDCl₃) δ 1.76 (6H, m), 2.20–2.92 (6H, m), 4.08–4.13 (1H, m), 4.18–4.21 (1H, m), 6.57–7.40 (8H, m).

This compound was then coupled to various acids, using a similar method to that of Example 7, to provide the compounds listed in Table III.

TABLE III

The compounds of the invention listed in Table III are compounds having the formula below wherein R⁵ is as defined in the Table.

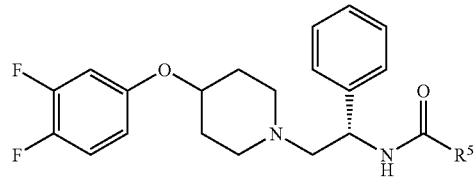

| Compound No. | R⁵ | M + H |
|---|---|---|
| 1 | 4-cyclohexyl-C₆H₄ | 519 |
| 2 | 4-n-butyl-C₆H₄ | 509 |
| 3 | 3-N(Me)₂—C₆H₄ | 480 |
| 4 | 4-NHC(O)Me—C₆H₄ | 494 |
| 5 | 4-N(Et)₂—C₆H₄ | 508 |
| 6 | 3-CO₂Me—C₆H₄ | 495 |
| 7 | 2-C(O)NH₂—C₆H₄ | 480 |
| 8 | 4-S(O)₂—C₆H₄ | 515 |
| 9 | 2-I—C₆H₄ | 563 |
| 10 | 3-phenoxy-C₆H₄ | 529 |
| 11 | 2-Me—C₆H₄ | 451 |
| 12 | 3-Me—C₆H₄ | 451 |
| 13 | 3-I—C₆H₄ | 563 |
| 14 | 2-NHC₆H₅-5-NH₂—C₆H₃ | 543 |
| 15 | 3,5-F₂—C₆H₃ | 473 |
| 16 | 3-NO₂-4-tert-butyl-C₆H₃ | 538 |
| 17 | 3-NO₂-5-CO₂Me—C₆H₃ | 540 |
| 18 | 2-Me-5-NO₂—C₆H₃ | 496 |
| 19 | 3,5-(tert-butyl)₂—C₆H₃ | 549 |
| 20 | 2-NO₂-5-Me—C₆H₃ | 496 |
| 21 | 2-NO₂5-SCN—C₆H₃ | 539 |
| 22 | 3-OMe-4-Me—C₆H₃ | 481 |
| 23 | 4-CN—C₆H₄ | 462 |
| 24 | 3-CN—C₆H₄ | 462 |
| 25 | 2-NH₂-5-I—C₆H₃ | 578 |
| 26 | 4-F—C₆H₄ | 455 |
| 27 | CH₂(2-NO₂—C₆H₄) | 496 |
| 28 | CH₂(2-Cl—C₆H₄) | 485 |
| 29 | CH₂(4-Cl—C₆H₄) | 485 |
| 30 | OCH₂C₆H₅ | 557 |
| 31 | CH₂CH₂(3,4-(OH)₂—C₆H₃) | 497 |
| 32 | CH₂(4-NO₂—C₆H₄) | 496 |
| 33 | (CH₂)₄C₆H₅ | 493 |
| 34 | CH₂(3,4-(OMe)—C₆H₃) | 511 |
| 35 | CH₂(4-OEt—C₆H₄) | 495 |
| 36 | CH₂(3-F-4-OH—C₆H₃) | 485 |
| 37 | (CH₂)₃C₆H₅ | 479 |
| 38 | CH₂(3,4-methylenedioxy-C₆H₃) | 495 |
| 39 | (CH₂)₃(4-OMe—C₆H₄) | 509 |
| 40 | (CH₂)₂(4-OH—C₆H₄) | 481 |
| 41 | CH₂(4-OH—C₆H₄) | 467 |
| 42 | CH₂(4-phenyl-C₆H₄) | 527 |
| 43 | (CH₂)₂(3-OH—C₆H₄) | 481 |
| 44 | (CH₂)₂(4-Me—C₆H₄) | 479 |
| 45 | (CH₂)₃(4-NO₂—C₆H₄) | 524 |
| 46 | (CH₂)₂(3,4-(OMe)₂—C₆H₃) | 525 |
| 47 | (CH₂)₃(4-Me—C₆H₄) | 493 |
| 48 | (CH₂)₂(C₆F₅) | 555 |
| 49 | (CH₂)₃(dibenzothiophen-2-yl) | 585 |
| 50 | CH₂(4-Me—C₆H₄) | 465 |
| 51 | (CH₂)₂(4-SH—C₆H₄) | 497 |
| 52 | CH₂(4-OCF₃—C₆H₄) | 535 |
| 53 | CH₂(4-OMe—C₆H₄) | 481 |
| 54 | CH₂(4-(O(CH₂(4-NO₂—C₆H₄)))—C₆H₄) | 602 |
| 55 | CH₂(3-F-4-OMe—C₆H₃) | 499 |
| 56 | (CH₂)₄(3-Me—C₆H₄) | 507 |
| 57 | CH₂(3-OH—C₆H₄) | 467 |
| 58 | CH₂(4-benzyloxy-C₆H₄) | 557 |
| 59 | CH₂(4-(3-NO₂—C₆H₄)—C₆H₄) | 572 |
| 60 | CH₂(2,5-Me₂—C₆H₃) | 479 |
| 61 | CH₂(4-I—C₆H₄) | 577 |
| 62 | CH₂(4-(4-(OCH(Me)CH(OH)CH₂CH₂-pyridin-3-yl)-C₆H₄)—C₆H₄) | 706 |
| 63 | CH₂(3-Br—C₆H₄) | 529 |
| 64 | (CH₂)₂(3-n-propyl-C₆H₄) | 507 |
| 65 | CH₂(2-Me-3-NO₂—C₆H₃) | 510 |
| 66 | CH₂(3-OH-4-OMe—C₆H₃) | 497 |
| 67 | CH₂(3-F—C₆H₄) | 469 |
| 68 | CH₂(2-F—C₆H₄) | 469 |

EXAMPLE 21

This Example illustrates the preparation of N-{2-[4-(3,4-dichlorophenoxy)-1-piperidinyl]ethyl}-2-[(methylsulfonyl)amino]benzamide hydrochloride.

Step a: 2-amino-N-{2-[4-(3,4-dichlorophenoxy)-1-piperidinyl]ethyl}benzamide dihydrochloride.

Prepared in a similar manner to Example 7 using the product of Example 3, Step b.

MS: APCI(+ve): 408(M+H).

¹H NMR (399.98 MHz, DMSO) δ 1.91–1.98 (2H, m), 2.15–2.26 (2H, m), 2.58 (2H, m), 3.18–3.29 (3H, m), 3.36 (2H, t), 3.57–3.68(2H, m), 3.72–3.79 (2H, m), 4.66 (1H, s), 6.63–6.71 (2H, m), 6.83 (1H, dd), 7.06 (1H, d), 7.22(1H, dt), 7.51 (1H, dd), 7.90 (1H, s).

Step b: N-{2-[4-(3,4-dichlorophenoxy)-1-piperidinyl]ethyl}-2-[(methylsulfonyl)amino]-benzamide hydrochloride.

Prepared in a similar manner to Example 18, Step b.

MS: APCI(+ve): 486(M+H)

¹HNMR(399.98 MHz, CDCl₃) δ 1.82(2H, m), 2.00(2H, m), 2.39(2H, m), 2.63(2H, t), 2.65(2H, m), 3.05(3H, s), 3.52(2H, q), 4.31(1H, m), 6.76(1H, dd), 7.00(1H, m), 7.15 (1H, m), 7.32(1H, d), 7.50(2H, m), 7.73(1H, dt)

EXAMPLE 22

This Example illustrates the preparation of 3-(aminosulfonyl)-N-{2-[4-(3,4-dichlorophenoxy)-1-piperidinyl]ethyl}benzamide.

Prepared in a similar manner to Example 7 using the product of Example 3, Step b.

MS: APCI(+ve): 472 (M+H)

¹H NMR (399.98 MHz, DMSO) δ 1.57–1.65 (2H, m), 1.91–1.94 (2H, m), 2.27–2.33 (2H, m), 2.48–2.52 (2H, m), 2.73–2.75 (2H, m), 3.40 (2H, q), 4.45 (1H, m), 6.98 (1H, dd), 7.26 (1H, d), 7.49 (3H, d), 7.67 (1H, t), 7.96 (1H, ddt), 8.03 (1H, tdt), 8.30 (1H, t), 8.65 (1H, t)

Melting point: 168–169° C.

EXAMPLE 23

This Example illustrates the preparation of N-{2-[4-(3,4-dichlorophenoxy)-1-piperidinyl]ethyl}-1-ethyl-7-methyl-4-oxo-1,4-dihydro[1,8]naphthyridine-3-carboxamide.

Prepared in a similar manner to Example 7 using the product of Example 3, Step b.

MS: APCI(+ve): 503 (M+H)

¹H NMR (299.946 MHz, DMSO) δ 1.25–1.68 (5H, m), 1.72–1.81 (2H, m), 1.88–1.95 (2H, m), 2.22 (3H, s), 2.31–2.40 (2H, m), 2.60–2.78 (3H, m), 2.92–3.00 (1H, m), 3.44–3.52 (1H, m), 4.36–4.49 (2H, m), 5.92–6.11 (1H, m), 6.91–7.06 (1H, m), 7.25 (1H, s), 7.30–7.41 (1H, m), 7.44–7.54 (1H, m), 11.86 (1H, s).

Melting point: 169–17° C.

EXAMPLE 24

This Example illustrates the preparation of N-{2-[4-(3,4-dichlorophenoxy)-1-piperidinyl]ethyl}-2-(4-hydroxyphenyl)acetamide.

Prepared in a similar manner to Example 7 using the product of Example 3, Step b.

MS: APCI(+ve):423 (M+H)

¹H NMR (399.98 MHz, DMSO) δ 1.53–1.61 (2H, m), 1.84–1.91 (2H, m), 2.17–2.24 (2H, m), 2.29–2.37 (2H, m), 2.60–2.70 (2H, m), 3.09–3.18 (2H, m), 3.28 (2H, s), 4.36–4.46 (1H, m), 6.62–6.72 (2H, m), 6.93–7.00 (1H, m), 7.00–7.08 (2H, m), 7.21–7.27 (1H, m), 7.43–7.53 (1H, m), 7.73–7.83 (1H, m), 9.25 (1H, s).

EXAMPLE 25

This Example illustrates the preparation of N-{2-[4-(3,4-dichlorophenoxy)-1-piperidinyl]ethyl}-2-[5-(1-pyrrolidinyl)-2H-tetraazol-2-yl]acetamide.

Prepared in a similar manner to Example 7 using the product of Example 3, Step b.

MS: APCI(+ve): 468 (M+H)

¹H NMR (399.98 MHz, DMSO) δ 1.56–1.63 (2H, m), 1.88–1.95 (6H, m), 2.22–2.27 (2H, m), 2.37–2.42 (2H, m), 2.65–2.72 (2H, m), 3.20–3.24 (2H, m), 3.31–3.37 (4H, m), 4.40–4.47 (1H, m), 5.19 (2H, s), 6.96–7.01 (1H, m), 7.24–7.27 (1H, m), 7.50 (1H, d), 8.15–8.24 (1H, m).

Melting point: 114–116° C.

EXAMPLE 26

This Example illustrates the preparation of N-{2-[4-(3,4-dichlorophenoxy)-1-piperidinyl]ethyl}-2-(2-methyl-4-phenyl-1,3-thiazol-5-yl)acetamide.

Prepared in a similar manner to Example 7 using the product of Example 3, Step b.

MS: APCI(+ve): 504 (M+H)

¹H NMR (299.946 MHz, DMSO) δ 1.54–1.63 (2H, m), 1.85–1.93 (2H, m), 2.21–2.28 (2H, m), 2.33–2.39 (2H, m), 2.62–2.71 (5H, m), 3.16–3.22 (2H, m), 3.74 (2H, s), 4.39–4.48 (1H, m), 6.94–7.00 (1H, m), 7.23–7.27 (1H, m), 7.34–7.50 (4H, m), 7.60–7.67 (2H, m), 8.08–8.15 (1H, m).

EXAMPLE 27

This Example illustrates the preparation of N-{2-[4-(3,4-dichlorophenoxy)-1-piperidinyl]ethyl}-5-(methylsulfonyl)-2-thiophenecarboxamide.

Prepared in a similar manner to Example 7 using the product of Example 3, Step b.

MS: APCI(+ve): 477 (M+H)

¹H NMR: (399.98 MHz DMSO) δ 1.54–1.65 (2H, m), 1.87–1.96 (2H, m), 2.24–2.34 (2H, m), 2.68–2.77 (2H, m), 3.34–3.42 (8H, m), 4.35–4.49 (1H, m), 7.25 (1H, d), 7.49 (1H,.d), 7.81 (2H, t), 8.80 (1H, t)

Melting point: 142–143° C.

EXAMPLE 28

This Example illustrates the preparation of N-{2-[4-(3,4-dichlorophenoxy)-1-piperidinyl]ethyl}-6-(1H-pyrazol-1-yl) nicotinamide.

Prepared in a similar manner to Example 7 using the product of Example 3, Step b.

MS: APCI(+ve):460 (M+H)

¹H NMR: (399.98 MHz DMSO) δ 1.54–1.69 (2H, m), 1.85–2.00 (2H, m), 2.23–2.37 (3H, m), 2.68–2.81 (2H, m), 3.34–3.47 (3H, m), 4.41–4.49 (1H, m), 6.60–6.64 (1H, m), 6.93–7.04 (1H, m), 7.26 (1H, d), 7.46–7.55 (1H, m), 7.89 (1H, d), 7.95–8.05 (1H, m), 8.32–8.42 (1H, m), 8.60–8.71 (2H, m), 8.85–8.92 (1H, m)

Melting point: 154–155° C.

EXAMPLE 29

This Example illustrates the preparation of N-{2-[4-(3,4-dichlorophenoxy)-1-piperidinyl]ethyl}-4-(methylsulfonyl) benzamide.

Prepared in a similar manner to Example 7 using the product of Example 3, Step b.

MS: APCI(+ve): 471 (M+H)

¹H NMR: (399.98 MHz DMSO) δ 1.55–1.67 (2H, m), 1.86–1.97 (2H, m), 2.24–2.35 (2H, m), 2.69–2.79 (2H, m), 3.35–3.46 (7H, m), 4.39–4.49 (1H, m), 6.94–7.03 (1H, m), 7.25 (1H, d), 7.49 (1H, d), 7.99–8.10 (4H, m), 8.66 (1H, t)

Melting point: 100–101° C.

EXAMPLE 30

This Example illustrates the preparation of N-{2-[4-(3,4-dichlorophenoxy)-1-piperidinyl]ethyl}imidazo[1,2-a] pyridine-2-carboxamide.

Prepared in a similar manner to Example 7 using the product of Example 3, Step b.

MS: APCI(+ve): 433 (M+H)

¹H NMR: (399.98 MHz DMSO) δ 1.53–1.70 (2H, m), 1.86–2.00 (2H, m), 2.23–2.34 (2H, m), 2.66–2.80 (2H, m), 3.27–3.35 (2H, m), 3.34–3.46 (2H, m), 4.41–4.50 (1H, m), 6.94–7.02 (2H, m), 7.26 (1H, d), 7.29–7.39 (1H, m), 7.46–7.53 (1H, m), 7.56–7.63 (1H, m), 8.22 (1H, t), 8.35 (1H, s), 8.52–8.67 (1H, m)

Melting point: 150–151° C.

EXAMPLE 31

This Example illustrates the preparation of 5-(2-chloroanilino)-N-{2-[4-(3,4-dichlorophenoxy)-1-piperidinyl]ethyl}-1,3,4-oxadiazole-2-carboxamide.

Step a: N-{2-[4-(3,4-dichlorophenoxy)piperidin-1-yl]ethyl}-2-hydrazino-2-oxoacetamide.

To a solution of the product of Example 3, Step b (0.85 g) and triethylamine (0.82 ml) at RT in dichloromethane (20 ml) was added methyl oxalyl chloride (0.30 ml) dropwise over 10 minutes. The reaction mixture was partitioned between water (20 ml) and dichloromethane (20 ml). The organic phase was separated and dried with $MgSO_4$. Evaporation under reduced pressure gave an oil which was dissolved in ethanol (10 ml) at RT and treated with hydrazine hydrate (1 ml) The reaction mixture was stirred at reflux for 24 hours, filtered and the filtrate evaporated under reduced pressure to leave an oil. Purification by flash chromatography (dichloromethane:methanol 90:10)gave the sub-title compound as a white solid (0.18 g).

MS: ESI(+ve): 375 (M+H)

Step b: 5-(2-chloroanilino)-N-{2-[4-(3,4-dichlorophenoxy)-1-piperidinyl]ethyl}-1,3,4-oxadiazole-2-carboxamide.

2-Chlorophenylisothiocyanate (0.102 g) was added to a stirred suspension of the compound from Step a (0.18 g) in dimethylformamide (5 ml) stirring at RT. After stirring for 1 hour, aminomethylated polystyrene (0.295 g) was added and the mixture stirred at RT for 16 hours. N-Cyclohexylcarbodiimide, and N'-methyl polystyrene (0.57 g) was then added and the mixture stirred at 80° C. for 2 hours. The reaction mixture was cooled to RT, filtered, and the resin washed with dimethylformamide (3×5 ml). The combined filtrates were evaporated and the residue triturated with diethyl ether, filtration gave the title compound as a white solid (0.14 g).

MS: APCI(+ve): 510 (M+H)
$^1$H NMR: (299.98 MHz DMSO) δ 1.51–1.70 (2H, m), 1.83–1.98 (2H, m), 2.19–2.37 (2H, m), 2.42–2.55 (1H, m), 2.63–2.81 (2H, m), 3.23–3.49 (3H, m), 4.32–4.53 (1H, m), 6.89–7.61 (6H, m), 7.88–8.01 (1H, m), 8.80–8.99 (1H, m), 10.32 (1H, s)

Melting point: 161–162° C.

EXAMPLE 32

This Example illustrates the preparation of N-{2-[4-(2-chloro-4-fluorophenoxy)-1-piperidinyl]ethyl}-6-(1H-pyrazol-1-yl)nicotinamide.

Step a: 4-(2-Chloro-4-fluorophenoxy)piperidine.

DEAD (0.90 ml) was added to a solution of triphenylphosphine (1.44 g), 2-chloro-4-fluorophenol (0.806 g) and 4-hydroxy-piperidine-1-carboxylic acid tert-butyl ester (1.0 g) in THF at RT. The reaction was stirred for 16 hrs, HCl (2 ml, 4M in dioxan) added and the mixture stirred at RT for 16 hrs. The mixture was then evaporated to dryness, triethylamine (5 ml) added, re-evaporated, dissolved in methanol (10 ml) and placed on to a SCX cartridge (Varian, 10 g), eluted first with methanol then with 10% $NH_3$ in methanol. The basic fractions were combined and evaporated to give the sub-title compound as an oil (0.98 g)

MS: ESI(+ve): 230 (M+H)).

Step b: 2-[4-(2-Chloro-4-fluorophenoxy)piperidin-1-yl]ethylamine.

Potassium carbonate (1.02 g, 0.0074 mol) was added to a solution of the 2-chloro-4-fluorophenoxypiperidine (1.7 g, 0.0074 mol) and tert-butyl 2-bromoethylcarbamate (1.65 g, 0.0074 mol) stirring at RT. The resulting mixture was stirred at RT for 24 hours, diluted with ethyl acetate (200 ml) and washed with saturated brine solution (3×100 ml). The organic layer was dried with $MgSO_4$ and evaporated under reduced pressure. The residual oil was redissolved in dichloromethane (200 ml), treated with TFA (20 ml) and the solution stirred at RT overnight, evaporation under reduced pressure and purification by flash chromatography (ethyl acetate) gave the sub-title compound as a colourless oil (1.1 g).

MS: ESI(+ve): 273 (M+H)).

Step c: N-{2-[4(2-Chloro-4-fluorophenoxy)-1-piperidinyl]ethyl}-6-(1H-pyrazol-1-yl)nicotinamide.

The title compound was prepared in a similar manner to Example 7 using the product of Example 32, step b.

MS: APCI(+ve): 444 (M+H)
$^1$H NMR: (299.98 MHz DMSO) δ 1.48–1.77 (2H, m), 1.79–1.99 (2H, m), 2.22–2.41 (2H, m), 2.45–2.57 (2H, m), 2.62–2.81 (2H, m), 3.37–3.50 (2H, m), 4.33–4.50 (1H, m), 6.53–6.66 (1H, m), 7.01–7.28 (2H, m), 7.33–7.47 (1H, m), 7.81–7.94 (1H, m), 7.94–8.08 (1H, m), 8.30–8.43 (1H, m), 8.56–8.74 (2H, m), 8.83–8.96 (1H, m)

Melting point: 109–110° C.

EXAMPLE 33

This Example illustrates the preparation of N-{2-[4-(2-chloro-4-fluorophenoxy)-1-piperidinyl]ethyl}-3-(methylsulfonyl)benzamide.

The title compound was prepared in a similar manner to Example 7 using the product of Example 32, step b.

MS: APCI(+ve): 455 (M+H)
$^1$H NMR: (299.946 MHz DMSO) δ 1.60–1.78 (2H, m), 1.83–1.98 (2H, m), 2.24–2.40 (2H, m), 2.66–2.75 (2H, m), 2.94–3.06 (1H, m), 3.28–3.33 (2H, m), 3.37–3.47 (4H, m), 4.36–4.50 (1H, m), 7.10–7.28 (2H, m), 7.37–7.46 (1H, m), 7.67–7.82 (1H, m), 8.03–8.11 (1H, m), 8.14–8.20 (1H, m), 8.33–8.39 (1H, m), 8.67–8.76 (1H, m)

Melting point: 50–51° C.

EXAMPLE 34

This Example illustrates the preparation of N-{2-[4-(2,4-dichloro-3-methylphenoxy)-1-piperidinyl]ethyl}-4-(methylsulfonyl)benzamide.

Step a: 4-(2,4-Dichloro-3-methylphenoxy)piperidine.

The sub-titled compound was prepared in a similar manner to Example 32, Step a.

MS: ESI(+ve): 260 (M+H)

Step b: 2-[4-(2,4-Dichloro-3-methylphenoxy)piperidin-1-yl]ethylamine.

The sub-titled compound was prepared in a similar manner to Example 32, Step b.

MS: ESI(+ve): 303 (M+H)

Step c: N-{2-[4-(2,4-Dichloro-3-methylphenoxy)-1-piperidinyl]ethyl}-4-(methylsulfonyl)benzamide.

The sub-titled compound was prepared in a similar manner to Example 7 using the product of Example 34, Step b.

MS: APCI(+ve): 485 (M+H)
$^1$H NMR: (299.98 MHz DMSO) δ 1.57–1.73 (2H, m), 1.81–1.99 (2H, m), 2.25–2.40 (6H, m), 2.61–2.80 (2H, m), 3.16–3.52 (6H, m), 4.37–4.56 (1H, m), 7.02–7.16 (1H, m), 7.26–7.41 (1H, m), 7.95–8.13 (4H, m), 8.57–8.74 (1H, m)

Melting point: 171–172° C.

EXAMPLE 35

This Example illustrates the preparation of N-{2-[4-(2,4-dichloro-3-methylphenoxy)-1-piperidinyl]ethyl}-5-(methylsulfonyl)-2-thiophenecarboxamide.

The title compound was prepared in a similar manner to Example 7 using the product of Example 34, step b.

MS: APCI(+ve): 491 (M+H)
$^1$H NMR: (299.98 MHz DMSO) δ 1.50–1.77 (2H, m), 1.79–2.05 (2H, m), 2.23–2.58 (6H, m), 2.60–2.81 (2H, m), 3.22–3.47 (6H, m), 4.35–4.65 (1H, m), 7.01–7.18 (1H, m), 7.26–7.44 (1H, m), 7.71–7.91 (2H, m), 8.68–8.91 (1H, m)

Melting point:177–178° C.

EXAMPLE 36

This Example illustrates the preparation of N-{2-[4-(2,4-dichloro-3-methylphenoxy)-1-piperidinyl]ethyl}-2-(methylsulfonyl)benzamide.

The title compound was prepared in a similar manner to Example 7 using the product of Example 34, step b.

MS: APCI(+ve): 485 (M+H)

$^1$H NMR: (399.98 MHz DMSO) δ 1.59–1.73 (2H, m), 1.84–1.99 (2H, m), 2.29–2.43 (6H, m), 2.62–2.79 (2H, m), 3.24–3.43 (6H, m), 4.42–4.61 (1H, m), 7.00–7.17 (1H, m), 7.28–7.43 (1H, m), 7.45–7.60 (1H, m), 7.64–7.83 (2H, m), 7.89–8.04 (1H, m), 8.53 (1H, t)

Melting point: 71–72° C.

EXAMPLE 37

This Example illustrates the preparation of N-{2-[4-(4-chloro-3-methylphenoxy)-1-piperidinyl]ethyl}-4-(methylsulfonyl)benzamide.

Step a: 4-(4-Chloro-3-methylphenoxy)piperidine.

The sub-titled compound was prepared in a similar manner to Example 32, Step a.

MS: ESI(+ve): 226 (M+H)

Step b: 2-[4-(4-Chloro-3-methylphenoxy)piperidin-1-yl]ethylamine.

The sub-titled compound was prepared in a similar manner to Example 32, Step b.

MS: ESI(+ve): 269 (M+H)

Step c: N-{2-[4-(4-Chloro-3-methylphenoxy)-1-piperidinyl]ethyl}-4-(methylsulfonyl)benzamide.

The title compound was prepared in a similar manner to Example 7 using the product of Example 37, Step b.

MS: APCI(+ve): 451 (M+H)

$^1$H NMR: (399.98 MHz DMSO) δ 1.53–1.67 (2H, m), 1.89–1.98 (2H, m), 2.23–2.32 (5H, m), 2.67–2.83 (2H, m), 3.22–3.34 (7H, m), 4.29–4.40 (1H, m), 6.74–6.84 (1H, m), 6.96 (1H, d), 7.26 (1H, d), 7.97–8.11 (4H, m), 8.66 (1H, t)

Melting point: 123–124° C.

EXAMPLE 38

This Example illustrates the preparation of N-{2-[4-(4-chloro-3-methylphenoxy)-1-piperidinyl]ethyl}-6-(1H-pyrazol-1-yl)nicotinamide.

The title compound was prepared in a similar manner to Example 7 using the product of Example 37, Step b.

MS: APCI(+ve): 440 (M+H)

$^1$H NMR: (399.98 MHz DMSO) δ 1.55–1.67 (2H, m), 1.83–2.03 (2H, m), 2.20–2.35 (6H, m), 2.69–2.87 (2H, m), 3.27–3.34 (1H, m), 3.36–3.50 (2H, m), 4.29–4.42 (1H, m), 6.55–6.67 (1H, m), 6.73–6.88 (1H, m), 6.96 (1H, d), 7.26 (1H, d), 7.89 (1H, d), 7.94–8.06 (1H, m), 8.29–8.42 (1H, m), 8.58–8.74 (2H, m), 8.80–8.94 (1H, m)

Melting point: 183–184° C.

EXAMPLE 39

This Example illustrates the preparation of N-{2-[$^4$-(4-chloro-3-methylphenoxy)-1-piperidinyl]ethyl}-2-(methylsulfonyl)benzamide.

The title compound was prepared in a similar manner to Example 7 using the product of Example 37, Step b.

MS: APCI(+ve): 451 (M+H)

$^1$H NMR: (399.98 MHz DMSO) δ 1.52–1.68 (2H, m), 1.83–2.00 (2H, m), 2.20–2.33 (5H, m), 2.68–2.79 (2H, m), 3.27–3.40 (7H, m), 4.30–4.42 (1H, m), 6.77–6.85 (1H, m), 6.92–6.99 (1H, m), 7.22–7.31 (1H, m), 7.48–7.56 (1H, m), 7.64–7.82 (2H, m), 7.93–8.00 (1H, m), 8.49–8.64 (1H, m)

Melting point: 63–64° C.

EXAMPLE 40

This Example illustrates the preparation of 3-(aminosulfonyl)-4-chloro-N-{2-[4-(3,4-difluorophenoxy)-1-piperidinyl]ethyl}benzamide.

The title compound was prepared in a similar manner to Example 7 using the product of Example 6, Step d.

MS: APCI(+ve): 474 (M+H)

$^1$H NMR: (399.98 MHz DMSO) δ 1.54–1.65 (2H, m), 1.86–1.97 (2H, m), 2.22–2.35 (2H, m), 2.64–2.82 (2H, m), 3.36–3.43 (2H, m), 4.29–4.41 (1H, m), 6.73–6.83 (1H, m), 7.03–7.14 (1H, m), 7.24–7.38 (1H, m), 7.70 (2H, s), 7.73–7.80 (3H, m), 7.98–8.06 (1H, m), 8.44 (1H, d), 8.68–8.75 (1H, m)

Melting point: 80–81° C.

EXAMPLE 41

This Example illustrates the preparation of 2-cyano-N-{2-[4-(3,4-difluorophenoxy)-1-piperidinyl]ethyl}benzamide.

The title compound was prepared in a similar manner to Example 7 using the product of Example 6, Step d.

MS: APCI(+ve): 386 (M+H)

$^1$H NMR: (399.98 MHz DMSO) δ 1.46–1.58 (2H, m), 1.78–1.94 (2H, m), 2.22–2.35 (2H, m), 2.54–2.63 (2H, m), 2.70–2.83 (2H, m), 3.79–3.89 (2H, m), 4.28–4.39 (1H, m), 6.72–6.81 (1H, m), 7.00–7.14 (1H, m), 7.23–7.37 (1H, m), 7.65–7.84 (3H, m), 8.15 (1H, d), 10.11 (1H, d)

Melting point: 146–147° C.

EXAMPLE 42

This Example illustrates the preparation of 2-chloro-N-{2-[4-(3,4-difluorophenoxy)-1-piperidinyl]ethyl}-4-(methylsulfonyl)benzamide.

The title compound was prepared in a similar manner to Example 7 using the product of Example 6, Step d.

MS: APCI(+ve): 473 (M+H)

$^1$H NMR: (399.98 MHz DMSO) δ 1.55–1.65 (2H, m), 1.88–1.97 (2H, m), 2.24–2.34 (2H, m), 2.69–2.79 (2H, m), 3.34–3.43 (7H, m), 4.31–4.42 (1H, m), 6.74–6.82 (1H, m), 7.03–7.16 (1H, m), 7.25–7.38 (1H, m), 7.68 (1H, t), 7.90–7.96 (1H, m), 8.04 (1H, d), 8.56 (1H, t)

Melting point: 108–109° C.

EXAMPLE 43

This Example illustrates the preparation of 3-cyano-N-{2-[4-(3,4-difluorophenoxy)-1-piperidinyl]ethyl}benzamide.

The title compound was prepared in a similar manner to Example 7 using the product of Example 6, Step d.

MS: APCI(+ve): 386 (M+H)

$^1$H NMR: (399.98 MHz DMSO) δ 1.54–1.65 (2H, m), 1.86–1.98 (2H, m), 2.22–2.34 (2H, m), 2.69–2.79 (2H, m), 3.35–3.45 (4H, m), 4.32–4.40 (1H, m), 6.74–6.81 (1H, m), 7.04–7.14 (1H, m), 7.25–7.37 (1H, m), 7.65–7.73 (1H, m), 7.97–8.03 (1H, m), 8.10–8.16 (1H, m), 8.25 (1H, t), 8.63 (1H, t)

Melting point: 106–107° C.

EXAMPLE 44

This Example illustrates the preparation of N-{2-[4-(3,4-difluorophenoxy)-1-piperidinyl]ethyl}-4-[(methylsulfonyl)methyl]benzamide.

The title compound was prepared in a similar manner to Example 7 using the product of Example 6, Step d.

MS: APCI(+ve): 453 (M+H)

$^1$H NMR: (399.98 MHz DMSO) δ 1.52–1.66 (2H, m), 1.69–1.77 (2H, m), 1.86–1.99 (2H, m), 2.22–2.33 (2H, m), 2.69–2.79 (2H, m), 2.88–2.95 (3H, m), 2.97–3.07 (2H, m), 4.29–4.41 (1H, m), 4.55 (2H, s), 6.69–6.86 (1H, m), 7.01–7.16 (1H, m), 7.22–7.36 (1H, m), 7.49 (2H, d), 7.84 (2H, d), 8.42 (1H, t)

Melting point: 115–116° C.

EXAMPLE 45

This Example illustrates the preparation of N-{2-[4-(3,4-difluorophenoxy)-1-piperidinyl]ethyl}-6-(1H-pyrazol-1-yl)nicotinamide.

The title compound was prepared in a similar manner to Example 7 using the product of Example 6, Step d.

MS: APCI(+ve): 428 (M+H)

$^1$H NMR: (399.98 MHz DMSO) δ 1.50–1.68 (2H, m), 1.83–2.01 (2H, m), 2.20–2.36 (2H, m), 2.69–2.83 (2H, m), 3.36–3.50 (4H, m), 4.28–4.45 (1H, m), 6.56–6.66 (1H, m), 6.73–6.83 (1H, m), 7.02–7.15 (1H, m), 7.25–7.38 (1H, m), 7.89 (1H, d), 7.96–8.06 (1H, m), 8.33–8.41 (1H, m), 8.60–8.73 (2H, m), 8.84–8.93 (1H, m)

Melting point:. 161–162° C.

EXAMPLE 46

Pharmacological Analysis: Calcium Flux $[Ca^{2+}]_i$ Assay

Human Eosinophils

Human eosinophils were isolated from EDTA anticoagulated peripheral blood as previously described (Hansel et al., *J. Immunol. Methods*, 1991, 145, 105–110). The cells were resuspended ($5 \times 10^6$ ml$^{-1}$) and loaded with 5 µM FLUO-3/AM+Pluronic F127 2.21 µl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at $2.5 \times 10^6$ ml$^{-1}$. The cells were then transferred to 96 well FLIPr plates (Poly-D-Lysine plates from Becton Dickinson pre-incubated with 5 µM fibronectin for two hours) at 25 µl/well. The plate was centrifuged at 200 g for 5 min and the cells were washed twice with LKS (200 µl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

Human Eosinophil Chemotaxis

Human eosinophils were isolated from EDTA anticoagulated peripheral blood as previously described (Hansel et al., *J. Immunol. Methods*, 1991, 145, 105–110). The cells were resuspended at $10 \times 10^6$ ml$^{-1}$ in RPMI containing 200 IU/ml penicillin, 200 µg/ml streptomycin sulphate and supplemented with 10% HIFCS, at room temperature.

Eosinophils (700 µl) were pre-incubated for 15 mins at 37° C. with 7 µl of either vehicle or compound (100× required final concentration in 10% DMSO). The chemotaxis plate (ChemoTx, 3 µm pore, Neuroprobe) was loaded by adding 28 µl of a concentration of eotaxin (0.1 to 100 nM) containing a concentration of a compound according to the Examples or solvent to the lower wells of the chemotaxis plate. The filter was then placed over the wells and 25 µl of eosinophil suspension were added to the top of the filter. The plate was incubated for 1 hr at 37° C. in a humidified incubator with a 95% air/15% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 µl of PBS containing 0.5% Triton x 100 followed by two cycles of freeze/thawing. The cell lysate was then added to the supernatant. The number of eosinophils migrating was quantified according to the method of Strath et al., *J. Immmunol. Methods*, 1985, 83, 209 by measuring eosinophil peroxidase activity in the supernatant.

Certain compounds of the Examples were found to be antagonists of the eotaxin mediated human eosinophil chemotaxis.

EXAMPLE 47

Guinea-pig Isolated Trachea (See for example, Harrison, R. W. S., Carswell, H. & Young, J. M. (1984) European J. Pharmacol., 106, 405–409.)

Male albino Dunlin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM): NaCl 117.6, NaH$_2$PO$_4$ 0.9, NaHCO$_3$ 25.0, MgSO$_4$ 1.2, KCl 5.4, CaCl$_2$ 2.6 and glucose 11.1. The buffer was maintained at 37° C. and gassed with 5% CO$_2$ in oxygen. Indomethacin (2.8 µM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 log$_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[A$_{50}$] values) of histamine in the absence and presence of the test compound. Affinity (pA$_2$) values of test compounds were subsequently calculated using the following equation:

$$\log(r-1) = \log[B] + pA_2$$

What is claimed is:

1. A compound of formula (I):

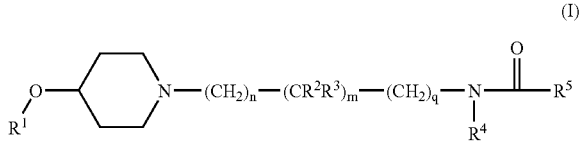

wherein

R¹ is phenyl optionally substituted by cyano, $S(O)_2(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy;

n is 1, 2, 3 or 4; m is 0; q is 0;

wherein $R^2$ and $R^3$ are, independently, hydrogen or $C_{1-6}$ alkyl, and $R^4$ is hydrogen, then $R^5$ is phenyl substituted at least once with a substituent selected from the group consisting of: $C_{1-6}$ alkyl substituted with at least one of $NH_2$, $CO_2(C_{1-6}$ alkyl), $S(O)_2(C_{1-6}$ alkyl), $NHS(O)_2$ $(C_{1-6}$ alkyl) and $S(O)_2NR^{13}R^{14}$, $S(O)_2(C_{1-6}$ alkyl), $S(O)_2(C_{1-6}$ hydroxyalkyl), $S(O)_2NH(C_{1-6}$ alkyl), NHC $(O)(C_{1-6}$ alkyl), $NHS(O)_2(C_{1-6}$ alkyl), $C_{1-6}$ alkoxy substituted with at least one of $C_{1-6}$ alkoxy, hydroxy, $CO_2(C_{1-6}$ alkyl), $NHC(O)O(C_{1-6}$ alkyl) and $NH_2$, $C_{2-6}$ alkenyl, pyrrolyl and $\Delta^3$-pyrrolinyl; and optionally further substituted with a substituent selected from the group consisting of: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido $(S(O)_2NH_2)$, (di)$C_{1-6}$ alkylsulphonamido, phenyl, phenylamino, nitrophenyl, pyridyl, pyridylthio, benzodioxanyl, thienyl, furanyl, and $C(O)R^{10}$-substituted $C_{1-6}$ alkyl or $C_{1-6}$ alkoxy groups; and when $R^2$ and $R^3$ are, independently, hydrogen or $C_{1-6}$ alkyl, and $R^4$ is $C_{1-4}$ alkyl or $C_{3-6}$ cycloalkyl($C_{1-4}$ alkyl), then $R^5$ is a phenyl optionally substituted by halogen, cyano, nitro, hydroxy, $C_{1-6}$ alkyl optionally substituted with one or more of halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2(C_{1-6}$ alkyl) and $S(O)_2NR^{13}R^{14}$, $C_{3-6}$ cycloalkyl, $C_{1-6}$ alkoxy substituted with at least one of halogen, $C_{1-6}$ alkoxy, hydroxy, $C(O)R^{10}$, $CO_2(C_{1-6}$ alkyl), $NHC(O)O(C_{1-6}$ alkyl) and $NH_2$, $C_{2-6}$ alkenyl, $C_{1-6}$ alkoxycarbonyl, $NR^6R^7$, $C_{3-6}$ cycloalkylamino, $C_{1-6}$ alkylthio, $C_{1-6}$ alkylcarbonylamino, $C(O)NR^8R^9$, sulphonamido $(S(O)_2NH_2)$, (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl;

$R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl;

or a pharmaceutically acceptable salt thereof; or a solvate thereof.

2. A compound of formula (I) as claimed in claim 1 wherein R¹ is phenyl optionally substituted by cyano, $S(O)_2$ $(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy; n is 1, 2, 3 or 4; m is 0; q is 0, $R^2$ and $R^3$ are, independently, hydrogen or $C_{1-6}$ alkyl; $R^4$ is hydrogen; $R^5$ is phenyl substituted at least once with a substituent selected from the group consisting of: $C_{1-6}$ alkyl substituted with at least one of $NH_2$, $CO_2(C_{1-6}$ alkyl), $S(O)_2(C_{1-6}$ alkyl), $NHS(O)_2(C_{1-6}$ alkyl) and $S(O)_2NR^{13}R^{14}$, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), $C_{1-6}$ alkoxy substituted with at least one of $C_{1-6}$ alkoxy, hydroxy, $CO_2(C_{1-6}$ alkyl), $NHC(O)O(C_{1-6}$ alkyl) and $NH_2$, $C_{2-6}$ alkenyl, pyrrolyl and $\Delta^3$-pyrrolinyl; and optionally further substituted with a substituent selected from the group consisting of: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido $(S(O)_2$ $NH_2)$, (di)$C_{1-6}$ alkylsulphonamido, phenyl, phenylamino, nitrophenyl, pyridyl, pyridylthio, benzodioxanyl, thienyl, furanyl, and $C(O)R^{10}$-substituted $C_{1-6}$ alkyl or $C_{1-6}$ alkoxy groups;

$R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

3. A compound of formula (I) as claimed in claim 1 wherein R¹ is phenyl optionally substituted by cyano, $S(O)_2$ $(C_{1-6}$ alkyl), $S(O)_2(C_{1-6}$ haloalkyl), halogen, $C_{1-6}$ alkyl, $C_{1-6}$ haloalkyl or $C_{1-6}$ alkoxy; n is 1, 2, 3 or 4; m is 0; q is 0, $R^2$ and $R^3$ are, independently, hydrogen or $C_{1-6}$ alkyl; $R^4$ is $C_{1-4}$ alkyl or $C_{3-6}$ cycloalkyl($C_{1-4}$ alkyl); $R^5$ is phenyl optionally substituted by halogen, cyano, nitro, hydroxy, $C_{1-6}$ alkyl optionally substituted with one or more of halogen, $C_{1-6}$ alkylthio, $NH_2$, $C(O)R^{10}$, $CO_2(C_{1-6}$ alkyl), $S(O)_2(C_{1-6}$ alkyl), $NHS(O)_2(C_{1-6}$ alkyl) and $S(O)_2NR^{13}R^{14}$, $C_{3-6}$ cycloalkyl, $C_{1-6}$ alkoxy substituted with at least one of halogen, $C_{1-6}$ alkoxy, hydroxy, $C(O)R^{10}$, $CO_2(C_{1-6}$ alkyl), $NHC(O)O(C_{1-6}$ alkyl) and $NH_2$, $C_{2-6}$ alkenyl, $C_{1-6}$ alkoxycarbonyl, $NR^6R^7$, $C_{3-6}$ cycloalkylamino, $C_{1-6}$ alkylthio, $C_{1-6}$ alkylcarbonylamino, $C(O)NR^8R^9$, sulphonamido $(S(O)_2NH_2)$, (di)$C_{1-6}$ alkylsulphonamido, $S(O)_2(C_{1-6}$ alkyl), $S(O)_2(C_{1-6}$ hydroxyalkyl), $S(O)_2NH(C_{1-6}$ alkyl), $NHC(O)(C_{1-6}$ alkyl), $NHS(O)_2(C_{1-6}$ alkyl), phenyl, phenylamino, nitrophenyl, pyridyl, pyridylthio, benzodioxanyl, thienyl, furanyl, pyrrolyl or $\Delta^3$-pyrrolinyl;

$R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

4. A compound of formula (I) as claimed in claim 1, wherein R¹ is phenyl optionally substituted by halogen, $C_{1-4}$ alkyl or $C_{1-4}$ alkoxy.

5. A compound of formula (I) as claimed in claim 1, wherein n is 2.

6. A compound of formula (I) as claimed in claim 1, wherein $R^4$ is hydrogen or $C_{1-4}$ alkyl; and $R^5$ is phenyl substituted by at least one of $C_{1-6}$ alkyl substituted with at least one of $S(O)_2(C_{1-6}$ alkyl), $NHS(O)_2(C_{1-6}$ alkyl) and $S(O)_2NR^{13}R^{14}$, $S(O)_2(C_{1-6}$ alkyl), $S(O)_2NH(C_{1-6}$ alkyl), $NHC(O)(C_{1-6}$ alkyl) or $NHS(O)_2(C_{1-6}$ alkyl); and optionally further substituted with a substituent selected from the group consisting of: halogen, cyano, nitro, hydroxy, $C_{1-6}$ alkyl, $C_{3-6}$ cycloalkyl, $C_{1-6}$ alkoxy, $C_{1-6}$ alkoxycarbonyl, $C_{1-6}$ haloalkyl, $C_{1-6}$ haloalkoxy, $NR^6R^7$, $C_{3-6}$ cycloalkylamino, $C_{1-6}$ alkylthio, $C_{1-6}$ alkylthio($C_{1-6}$ alkyl), $C_{1-6}$ alkylcarbonylamino, $C(O)NR^8R^9$, sulphonamido $(S(O)_2$ $NH_2)$, (di)$C_{1-6}$ alkylsulphonamido and $C(O)R^{10}$-substituted $C_{1-6}$ alkyl or $C_{1-6}$ alkoxy groups; $R^{10}$ is hydroxy or $NR^{11}R^{12}$ group; and, $R^6$, $R^7$ $R^8$, $R^9$, $R^{11}$, $R^{12}$, $R^{13}$ and $R^{14}$ are independently hydrogen or $C_{1-6}$ alkyl.

7. A process for preparing a compound of formula (I) as claimed in claim 1 comprising reacting a compound of formula (III):

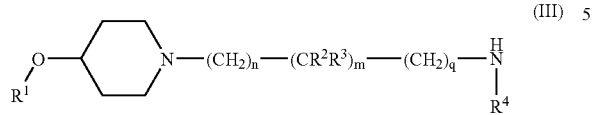
(III)

with a compound of formula (IV):

(IV)

wherein L is a leaving group.

8. A pharmaceutical composition which comprises a compound of the formula (I), or a pharmaceutically acceptable salt thereof or a solvate thereof, and a pharmaceutically acceptable adjuvant, diluent or carrier.

9. A method of treating chronic obstructive pulmonary disease, asthma, bronchitis, respiratory tract allergy, rhinitis, sarcoidosis, farmer's lung, nasal polyposis, fibroid lung, idiopathic interstitial pneumonia, chronic cough, iatrogenic induced cough, comprising administering to a patient in need of such treatment an effective amount of a compound of formula (I) as claimed in claim 1.

* * * * *